United States Patent
Levin et al.

(10) Patent No.: US 6,498,167 B2
(45) Date of Patent: Dec. 24, 2002

(54) PREPARATION AND USE OF ORTHO-SULFONAMIDO BICYCLIC HETEROARYL HYDROXAMIC ACIDS AS MATRIX METALLOPROTEINASE AND TACE INHIBITORS

(75) Inventors: Jeremy I. Levin, Nanuet, NY (US); Arie Zask, New York, NY (US); Yansong Gu, Pearl River, NY (US); Jay D. Albright, Nanuet, NY (US); Xuemei Du, Valley Cottage, NY (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/734,056

(22) Filed: Dec. 11, 2000

(65) Prior Publication Data

US 2001/0025047 A1 Sep. 27, 2001

Related U.S. Application Data

(60) Division of application No. 09/059,554, filed on Apr. 14, 1998, now Pat. No. 6,228,869, which is a continuation-in-part of application No. 09/055,856, filed on Apr. 6, 1998, now abandoned, which is a continuation-in-part of application No. 08/944,188, filed on Oct. 6, 1997, now abandoned.
(60) Provisional application No. 60/028,505, filed on Oct. 16, 1996.

(51) Int. Cl.⁷ ............................ A61K 31/56; C07D 7/00
(52) U.S. Cl. ........................ 514/310; 546/143; 546/159; 514/311; 514/314
(58) Field of Search ................................ 546/143, 159; 514/310, 311, 313, 314

(56) References Cited

U.S. PATENT DOCUMENTS

| 5,455,258 A | 10/1995 | MacPherson et al. |
| 5,506,242 A | 4/1996 | MacPherson et al. |
| 5,552,419 A | 9/1996 | MacPherson et al. |

FOREIGN PATENT DOCUMENTS

| EP | 0606046 | 7/1994 |
| EP | 780386 | 6/1997 |
| EP | 0757984 | 2/1999 |
| WO | WO 9535275 | 12/1995 |
| WO | WO 9535276 | 12/1995 |
| WO | WO 9600214 | 1/1996 |
| WO | WO 9627583 | 9/1996 |
| WO | WO 9633172 | 10/1996 |
| WO | WO 9640101 | 12/1996 |
| WO | WO 9718194 | 5/1997 |
| WO | WO 9719068 | 5/1997 |
| WO | WO 9720824 | 6/1997 |
| WO | WO 9722587 | 6/1997 |
| WO | WO 9724117 | 7/1997 |
| WO | WO 9727174 | 7/1997 |

OTHER PUBLICATIONS

J. Med. Chem., 40 2525–2532, Mac Pherson et al. (1997).

*Primary Examiner*—Sabiha Qazi
(74) *Attorney, Agent, or Firm*—Joy S. Goudie

(57) ABSTRACT

This invention provides low molecular weight, non-peptide inhibitors of matrix metalloproteinases and TNF-α converting enzyme (TACE, tumor necrosis factor-α converting enzyme) of formula (B) as shown herein or a pharmaceutically acceptable salt thereof.

8 Claims, No Drawings

PREPARATION AND USE OF ORTHO-SULFONAMIDO BICYCLIC HETEROARYL HYDROXAMIC ACIDS AS MATRIX METALLOPROTEINASE AND TACE INHIBITORS

This application is a divisional application of U.S. Ser. No. 09/059,554, filed Apr. 14, 1998, now U.S. Pat. No. 6,228,869 B1, issued May 8, 2001, which is a continuation-in-part of U.S. Ser. No. 09/055,856, filed on Apr. 6, 1998, now abandoned, which is a continuation in part of U.S. Ser. No. 08/944,188, filed on Oct. 6, 1997, now abandoned, which claims the benefit of priority to U.S. Provisional Application No. 60/028,505, filed Oct. 16, 1996.

BACKGROUND

The present invention relates to the discovery of novel, low molecular weight, non-peptide inhibitors of matrix metalloproteinases (e.g. gelatinases, stromelysins and collagenases) and TNF-α converting enzyme (TACE, tumor necrosis factor-α converting enzyme) which are useful for the treatment of diseases in which these enzymes are implicated such as arthritis, tumor metastasis, tissue ulceration, abnormal wound healing, periodontal disease, bone disease, proteinuria, aneurysmal aortic disease, degenerative cartilage loss following traumatic joint injury, demyelinating diseases of the nervous system and HIV infection.

Matrix metalloproteinases (MMPs) are a group of enzymes that have been implicated in the pathological destruction of connective tissue and basement membranes [Woessner, J. F., Jr. *FASEB J.* 1991, 5, 2145; Birkedal-Hansen, H.; Moore, W. G. I.; Bodden, M. K.; Windsor, L. J.; Birkedal-Hansen, B.; DeCarlo, A.; Engler, J. A. *Crit. Rev. Oral Biol. Med.* 1993, 4, 197; Cawston, T. E. *Pharmacol. Ther.* 1996, 70, 163; Powell, W. C.; Matrisian, L. M. *Cur. Top. Microbiol. and Immunol.* 1996, 213, 1]. These zinc containing endopeptidases consist of several subsets of enzymes including collagenases, stromelysins and gelatinases. Of these classes, the gelatinases have been shown to be the MMPs most intimately involved with the growth and spread of tumors, while the collagenases have been associated with the pathogenesis of osteoarthritis [Howell, D. S.; Pelletier, J.-P. In *Arthritis and Allied Conditions;* McCarthy, D. J.; Koopman, W. J., Eds.; Lea and Febiger: Philadelphia, 1993; 12*th Edition* Vol. 2, pp. 1723; Dean, D. D. *Sem. Arthritis Rheum.* 1991, 20, 2; Crawford, H. C; Matrisian, L. M. *Invasion Metast.* 1994–95, 14, 234; Ray, J. M.; Stetler-Stevenson, W. G. *Exp. Opin. Invest. Drugs,* 1996, 5, 323].

It is known that the level of expression of gelatinase is elevated in malignancies, and that gelatinase can degrade the basement membrane which may lead to tumor metastasis [Powell, W. C.; Matrisian, L. M. *Cur. Top. Microbiol. and Immunol.* 1996, 213, 1; Crawford, H. C; Matrisian, L. M. *Invasion Metast.* 1994–95, 14, 234; Ray, J. M.; Stetler-Stevenson, W. G. *Exp. Opin. Invest. Drugs,* 1996, 5, 323; Himelstein, B. P.; Canete-Soler, R.; Bernhard, E. J.; Dilks, D. W.; Muschel, R. J. *Invasion Metast.* 1994–95, 14, 246; Nuovo, G. J.; MacConnell, P. B.; Simsir, A.; Valea, F.; French, D. L. *Cancer Res.* 1995, 55, 267–275; Walther, M. M.; Levy, A.; Hurley, K.; Venzon, D.; Linehen, W. M.; Stetler-Stevenson, W. *J. Urol.* 1995, 153 (*Suppl.* 4), 403A; Tokuraku, M; Sato, H.; Murakami, S.; Okada, Y.; Watanabe, Y.; Seiki, M. *Int. J. Cancer,* 1995, 64, 355; Himelstein, B.; Hua, J.; Bernhard, E.; Muschel, R. J. *Proc. Am. Assoc. Cancer Res. Ann. Meet.* 1996, 37, 632; Ueda, Y.; Imai, K.; Tsuchiya, H.; Fujimoto, N.; Nakanishi, I.; Katsuda, S.; Seiki, M.; Okada, Y. *Am. J. Pathol.* 1996, 148, 611; Gress, T. M.; Mueller-Pillasch, F.; Lerch, M. M.; Friess, H.; Buechler, M.; Adler, G. *Int. J. Cancer,* 1995, 62, 407; Kawashima, A.; Nakanishi, I.; Tsuchiya, H.; Roessner, A.; Obata, K.; Okada, Y. *Virchows Arch.,* 1994, 424, 547–552.]. Angiogenesis, required for the growth of solid tumors, has also recently been shown to have a gelatinase component to its pathology [Crawford, H. C; Matrisian, L. M. *Invasion Metast.* 1994–95, 14, 234; Ray, J. M.; Stetler-Stevenson, W. G. *Exp. Opin. Invest. Drugs,* 1996, 5, 323.]. Furthermore, there is evidence to suggest that gelatinase is involved in plaque rupture associated with atherosclerosis [Dollery, C. M.; McEwan, J. R.; Henney, A. M. *Circ. Res.* 1995, 77, 863; Zempo, N.; Koyama, N.; Kenagy, R. D.; Lea, H. J.; Clowes, A. W. *Arterioscler. Thromb. Vasc. Biol.* 1996, 16, 28; Lee, R. T.; Schoen, F. J.; Loree, H. M.; Lark, M. W., Libby, P. *Arterioscler. Thromb. Vasc. Biol.* 1996, 16, 1070.]. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

The hypothesis that MMPs are important mediators of the tissue destruction that occurs in arthritis has long been considered, since it was first recognized that these enzymes are capable of degrading collagens and proteoglycans which are the major structural components of cartilage [Sapolsky, A. I.; Keiser, H.; Howell, D. S.; Woessner, J. F., Jr.; *J. Clin. Invest.* 1976, 58, 1030; Pelletier, J.-P.; Martel-Pelletier, J.; Howell, D. S.; Ghandur-Mnaymneh, L.; Enis, J. E.; Woessner, J. F., Jr., *Arthritis Rheum.* 1983, 26, 63.], and continues to develop as new MMPs are identified. For example, collagenase-3 (MLMP-13) was cloned from breast cancer cells in 1994, and the first report that it could be involved in arthritis appeared in 1995 [Freiji, J. M.; Diez-Itza, I.; Balbin, M.; Sanchez, L. M.; Blasco, R.; Tolivia, J.; Lopez-Otin, C. *J. Biol. Chem.* 1994,269, 16766; Flannery, C. R.; Sandy, J. D. 102–17, 41*st Ann. Meet. Orth. Res. Soc.* Orlando, Fla. Feb. 13–16, 1995.]. Evidence is accumulating that implicates MMP-13 in the pathogenesis of arthritis. A major structural component of articular cartilage, type II collagen, is the preferred substrate for MMP-13 and this enzyme is significantly more efficient at cleaving type II collagen than the other collagenases [Knauper, V.; Lopez-Otin, C.; Smith, B.; Knight, G.; Murphy, G. *J. Biol. Chem.,* 1996, 271, 1544–1550; Mitchell, P. G.; Magna, H. A.; Reeves, L. M.; Lopresti-Morrow, L. L.; Yocum, S. A.; Rosner, P. J.; Geoghegan, K. F.; Hambor, J. E. *J. Clin. Invest.* 1996, 97, 761.]. MMP-13 is produced by chondrocytes, and elevated levels of MMP-13 has been found in human osteoarthritic tissues [Reboul, P.; Pelletier, J-P.; Hambor, J.; Magna, H.; Tardif, G.; Cloutier, J-M.; Martel-Pelletier, J. *Arthritis Rheum.* 1995, 38 (*Suppl.* 9), S268;Shlopov, B. V.; Mainardi, C. L.; Hasty, K. A. *Arthritis Rheum.* 1995, 38 (*Suppl.* 9), S313; Reboul, P.; Pelletier, J-P.; Tardif, G.; Cloutier, J-M.; Martel-Pelletier, J. *J. Clin. Invest.* 1996, 97, 2011]. Potent inhibitors of MMPs were described over 10 years ago, but the poor bioavailability of these early peptidic, substrate mimetic MMP inhibitors precluded their evaluation in animal models of arthritis. More bioavailable, non-peptidic MMP inhibitors may be preferred for the treatment of diseases mediated by MMPs.

TNF-α converting enzyme catalyzes the formation of TNF-α from membrane bound TNF-α precursor protein. TNF-α is a pro-inflammatory cytokine that is now thought to have a role in rheumatoid arthritis, septic shock, graft rejection, insulin resistance and HIV infection in addition to its well documented antitumor properties. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. *Br. J. Rheumatol.* 1995, 34, 334; *Pharmaprojects,* 1996, Therapeutic Updates 17 (Oct.), 197. This observation has recently been extended to humans as well. Other conditions mediated by TNF-α are congestive heart failure, cachexia, anorexia, inflammation, fever, inflammatory disease of the central nervous system, and inflammatory bowel disease.

It is expected that small molecule inhibitors of gelatinase and TACE therefore have the potential for treating a variety of disease states. While a variety of MMP and TACE inhibitors have been identified and disclosed in the literature, the vast majority of these molecules are peptidic or peptide-like compounds that may have bioavailability and pharmacokinetic problems that would limit their clinical effectiveness. Low molecular weight, potent, long-acting, orally bioavailable inhibitors of gelatinases, collagenases and/or TACE are therefore highly desirable for the potential chronic treatment of the above mentioned disease states. Several non-peptide, sulfur-containing hydroxamic acids have recently been disclosed and are listed below.

U.S. Pat. Nos. 5,455,258, 5,506,242 and 5,552,419, as well as European patent application EP606,046A1 and WIPO international publications WO96/00214 and WO97/22587 disclose non-peptide matrix metalloproteinase inhibitors of which the compound CGS27023A is representative. The discovery of this type of MMP inhibitor is further detailed by MacPherson, et. al. in *J. Med. Chem.,* (1997),40, 2525. Additional publications disclosing sulfonamide based MMP inhibitors which are variants of the sulfonamide-hydroxamate shown below, or the analogous sulfonamide-carboxylates, are European patent application EP-757984-A1 and WIPO international publications WO95/35275, WO95/35276, WO96/27583, WO97/19068 and WO97/27174.

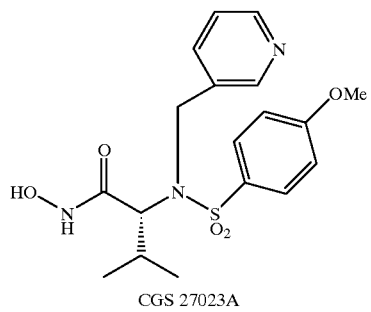

CGS 27023A

Publications disclosing β-sulfonamide-hydroxamate MMP inhibitor analogs of CGS 27023A in which the carbon alpha to the hydroxamic acid has been joined in a ring to the sulfonamide nitrogen, as shown below, include WIPO international publications WO96/33 172 and WO97120824.

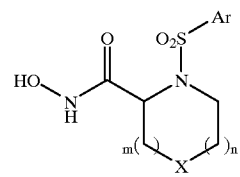

The German patent application DE19,542,189-A1 discloses additional examples of cylic sulfonamides as MMP inhibitors. In this case the sulfonamide-containing ring is fused to a phenyl ring to form an isoquinoline.

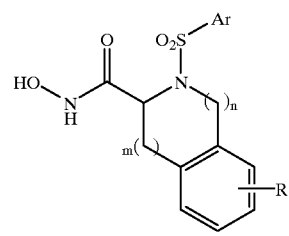

Analogs of the sulfonamide-hydroxamate MMP inhibitors in which the sulfonamide nitrogen has been replaced by a carbon atom, as shown in the general structure below, are European patent application EP-780386-A1 and WIPO international publication WO97/24117.

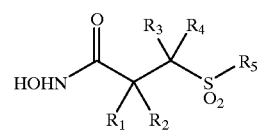

DESCRIPTION OF THE INVENTION

This invention provides TACE and MMP inhibitors having the formula

B wherein

B is

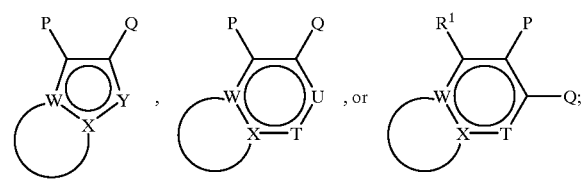

P and Q are

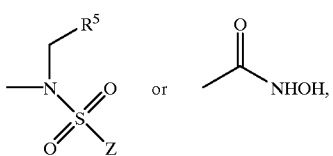

provided that when P is

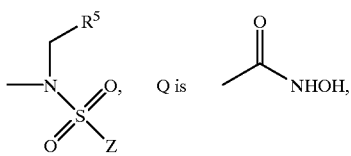 Q is and vice versa;
T, U, W, and X are each, independently, carbon or nitrogen, provided that when T or U is carbon, either may be optionally substituted with $R^1$;
Y is carbon, nitrogen, oxygen or sulfur, provided that at least one of T, U, W, X, and Y is not carbon, and further provided that no more than 2 of T, U, W, and X are nitrogen;

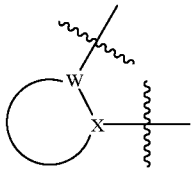

is a phenyl ring or is a heteroaryl ring of ring 5–6 atoms which may contain 0–2 heteratoms selected from nitrogen, oxygen, and sulfur, in addition to any heteroatoms defined by W or X; wherein the phenyl or heteroaryl ring may be optionally mono-, di-, or tri-substituted with $R^1$;
Z is a phenyl, naphthyl, heteroaryl, or heteroaryl fused to phenyl, wherein the heteroaryl moiety contains of 5–6 ring atoms and 1–3 heteroatoms selected from nitrogen, oxygen, or sulfur; wherein the phenyl, naphthyl, heteroaryl, or phenyl fused heteroaryl moieties may be optionally mono-, di-, or tri-substituted with $R^1$;
$R^1$ is hydrogen, halogen, alkyl of 1–8 carbon atoms, alkenyl of 2–6 carbon atoms, alkynyl of 2–6 carbon atoms, cyclocalkyl of 3–6 carbon atoms, —$(CH_2)_nZ$, —$OR^2$, —CN, —$COR^2$, perfluoroalkyl of 1–4 carbon atoms, —$CONR^2R^3$, —$S(O)_xR^2$ —$OPO(OR^2)OR^3$, —$PO(OR^2)R^3$, —$OC(O)NR^2R^3$, —$COOR^2$, —$CONR^2R^3$, —$SO_3H$, —$NR^2R^3$, —$NR^2COR^3$, —$NR^2COOR^3$, —$SO_2NR^2R^3$, —$NO_2$, —$N(R^2)SO_2R^3$, —$NR^2CONR^2R^3$, —$NR^2C(=NR^3)NR^2R^3$, —$SO_2NHCOR^4$, —$CONHSO_2R^4$, -tetrazol-5-yl, —$SO_2NHCN$, —$SO_2NHCONR^2R^3$, or Z;
V is a saturated or partially unsaturated heterocycloalkyl ring of 5–7 ring atoms having 1–3 heteroatoms selected from N, O, or S, which may be optionally mono-, or di-substituted with $R^2$;
$R^2$ and $R^3$ are each, independently, hydrogen, alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;
$R^4$ is alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;
$R^5$ is hydrogen, alkyl of 1–8 carbon atoms, alkenyl of 2–6 carbon atoms, alkynyl of 2–6 carbon atoms, Z, or V;
n=1–6;
X=0–2
or a pharmaceutically acceptable salt thereof.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

Alkyl, alkenyl, alkynyl, and perfluoroalkyl include both straight chain as well as branched moieties. The definitions of alkyl, alkenyl, alkynyl, and cycloalkyl include alkyl, alkenyl, alkynyl, and cycloalkyl moieties which are unsubstituted (carbons bonded to hydrogen, or other carbons in the chain or ring) or may be mono- or poly-substituted with $R^1$. Halogen means bromine, chlorine, fluorine, and iodine. Preferred heteroaryl rings include pyrrole, furan, thiophene, pyridine, pyrimidine, pyridazine, pyrazine, triazole, pyrazole, imidazole, isothiazole, thiazole, isoxazole and oxazole. Preferred "heteroaryl fused to phenyl" rings indole, isoindole, benzofuran, benzothiophene, quinoline, isoquinoline, quinoxaline, quinazoline, benzotriazole, indazole, benzimidazole, benzothiazole, benzisoxazole, and benzoxazole. The term "saturated or partially unsaturated heterocycloalkyl ring" means a saturated or partially unsaturated (but not aromatic, or fully saturated) heterocycle having 5–7 ring atoms, and containing 1–3 heteroatoms selected from N, O, or S. Preferred saturated or partially unsaturated heterocycloalkyl rings include piperidine, piperazine, morpholine, tetrahydropyran, thiomorpholine, or pyrrolidine. When a moiety contains more than substituent with the same designation (i.e., phenyl tri-substituted with $R^1$) each of those substituents ($R^1$ in this case) may be the same or different.

The compounds of this invention may contain an asymmetric carbon atom and some of the compounds of this invention may contain one or more asymmetric centers and may thus give rise to optical isomers and diastereomers. While shown without respect to stereochemistry in B, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are those in which:
B is

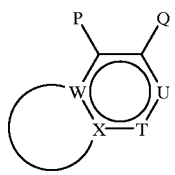

or a pharmaceutically acceptable salt thereof.

More preferred compounds of this invention are those in which:
B is

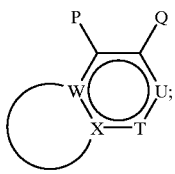

W and X are carbon; and
T is nitrogen;
U is carbon, optionally substituted with $R^1$
or a pharmaceutically acceptable salt thereof.

Still more preferred compounds of this invention are those in which:
B is

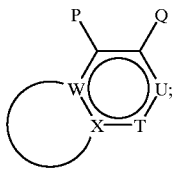

W and X are carbon; and
T is nitrogen;
U is carbon, optionally substituted with $R^1$
P is

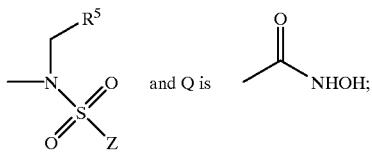

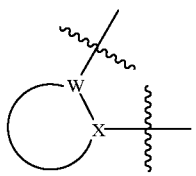

is phenyl or pyrazole, each optionally mono-, di-, or tri-substituted with $R^1$;
or a pharmaceutically acceptable salt thereof.

When $R^5$ is Z, it is preferred that Z is phenyl or pyridyl, each optionally mono-, di-, or tri-substituted with $R^1$.

It is preferred that the Z moiety bonded to the sulfur of the sulfonamide of B, is phenyl optionally mono-substituted with $R^1$ and $R^1$ is $OR^2$ or Z. When $R^1$ is Z it is preferred that Z is phenyl, or pyridyl, each optionally mono-, di-, or tri-substituted with $R^1$. When $R^1$ is $OR^2$, it is preferred that $R^2$ is alkyl of 1–8 carbon atoms or Z, with Z being phenyl or pyridyl, each optionally mono-, di-, or tri-substituted with $R^1$.

The compounds of this invention can be prepared according to the following schemes from commercially available starting materials or starting materials which can be prepared using to literature procedures. Typical known starting materials are shown below (I–XXI). These schemes, which follow thereafter, show the preparation of representative compounds of this invention.

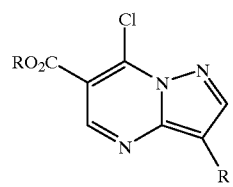

I

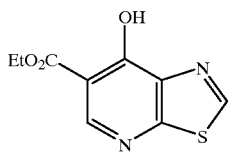

II

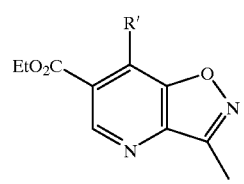

III

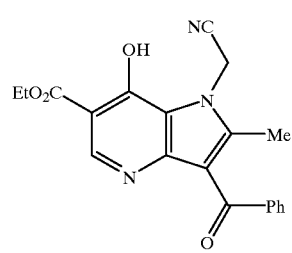

IV

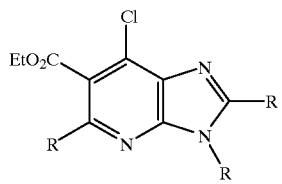

V

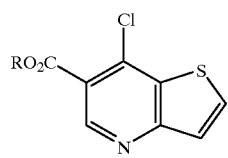

VI

-continued

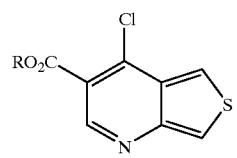 VII

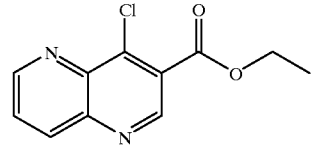 XVI

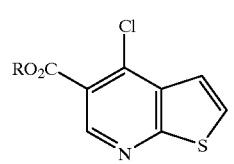 VIII

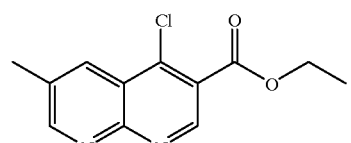 XVII

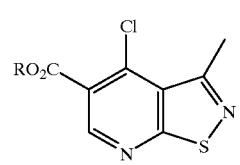 IX

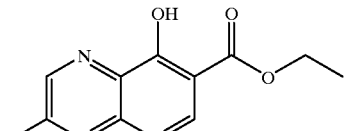 XVIII

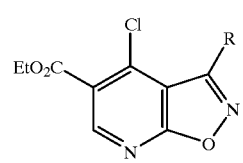 X

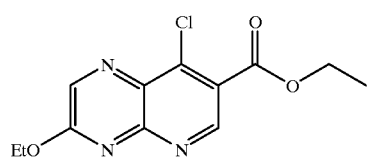 XIX

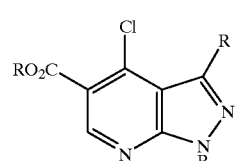 XI

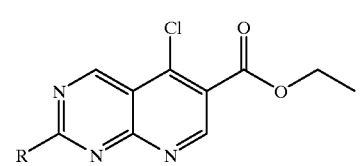 XX

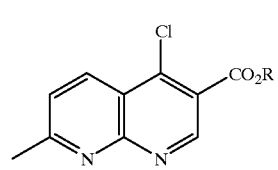 XII

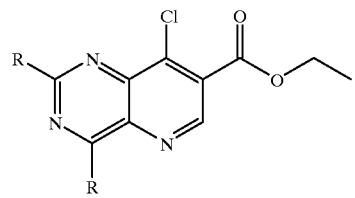 XXI

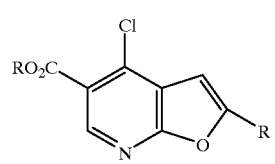 XIII

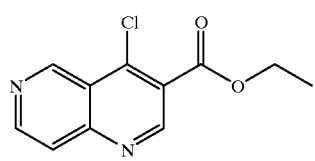 XIV

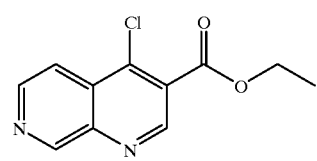 XV

Compound I:
  a) Springer, R H; Scholten, M B; O'Brien, D E, Novinson, T; Miller, J P; Robins, R K J. Med. Chem. (1982), 25(3), 235–42.
  b) Elworthy, T. R.; Ford, A. P. D.; et.al. J. Med. Chem. (1997), 40(17), 2674–2687.
Compound II:
  Masui, T; TAkura, T; JP 46043792; JP 690307; CAN 76:59604
Compound III:
  Camparini, A; Ponticelli, F; Tedeschi, P J. Chem. Soc., Perkin Trans.1 (1982), 10, 2391–4.
Compound IV:
  Abdalla, G M; Sowell. J W J. Heterocycl. Chem. (1990), 27 (5), 1201–7.
Compound V:
  a) Denzel, T; Hoehn, H J. Heterocyclic Chem. (1977), 14, 813–817.
  b) Al-Shaar, A H M; Chambers, R K; Gilmour, D W; Lythgoe, D J; McClenaghan, I; Ramsden, C A J. Chem. Soc.; Perkin Trans. I (1992) 21, 2789–2812.
  c) Elworthy, T. R.; Ford, A. P. D.; et.al J. Med. Chem. (1997), 40(17), 2674–2687.

Compound VI:
a) Forbes, I T; Johnson, C N; Jones, G E; Loudon, J; Nicholass, J M J. Med. Chem (1990) 2640–2645.
b) Kan, M A; Guarconi, A E J. Heterocyclic Chem (1977) 14, 807–812.

Compound VII:
a) Forbes, I T; Johnson, C N; Jones, G E; Loudon, J; Nicholass, J M J. Med. Chem (1990) 2640–2645.
b) Kan, M A; Guarconi, A E J. Heterocyclic Chem (1977) 14, 807–812.

Compound VIII:
Richardson, T O; Neale, N; Carwell, N J. Heterocyclic. Chem. (1995), 32, 359–361.
Baker, J M; Huddleston, P R; Keenan, G J J. Chem Research Miniprint, (1982) 6, 1726–1746.

Compound IX:
a) Forbes, I T; Johnson, C N; Jones, G E; Loudon, J; Nicholass, J M J. Med. Chem (1990) 2640–2645.
b) Kan, M A; Guarconi, A E J. Heterocyclic Chem (1977) 14, 807–812.

Compounds X, XI and XII:
Elworthy, T. R.; Ford, A. P. D.; et.al. J. Med. Chem. (1997), 40(17), 2674–2687.

Compound XIII:
Heterocycles, (1997), 45, 980.

Compound XIV:
Yokoyama, Naokata. Eur. Pat. Appl., 61 pp. CODEN: EPXXDW. EP 115469 A1 840808.

Compound XV:
Mendes, Etienne; Vernieres, Jean Claude; Simiand, Jacques Edouard; Keane, Peter Eugene. Eur. Pat. Appl., 12 pp. CODEN: EPXXDW. EP 346207 A1 891213.

Compound XVI:
Mendes, Etienne; Vernieres, Jean Claude; Simiand, Jacques Edouard; Keane, Peter Eugene. Eur. Pat. Appl., 12 pp. CODEN: EPXXDW. EP 346207 A1 891213.

Compound XVII:
Morita, Yoshiharu; Wagatsuma, Kazuo. Japan. Kokai, 4 pp. CODEN: JKXXAF. JP 50058094 750520 Showa.

Compounds XVIII and XIX:
Armitage, Bernard John; Leslie, Bruce William; Miller, Thomas Kerr; Morley, Christopher. PCT Int. Appl., 110 pp. CODEN: PIXXD2. WO 9500511 A1 950105.

Compound XX:
Minani, S.; Matsumoto, J.; Kawaguchi, K.; Mishio, S.; Shimizu, M.; Takase, Y.; Nakamura, S. (Dainippon Pharmaceutical Co., Ltd., Japan) Japan. Kokai, 3pp. CODEN: JKXXAF. JP 50014697 750215 Showa.

Compound XXI:
Kihara, N.; Tan, H.; Takei, M.; Ishihara, T. (Mitsui Pechochemical Industries, Ltd., Japan; Suntory, Ltd.) Jpn. Kokai Tokyo Koho, 11 pp. CODEN: JKXXAF. JP 62221686 A2 870929 Showa.

The compounds of this invention can be prepared using conventional techniques known to those skilled in the art of organic synthesis. The following scheme (Scheme I) illustrates the reaction sequence employed. In the schemes which follow, the moiety A is defined as the bicyclic heteroaryl moiety of B, as shown immediately below:

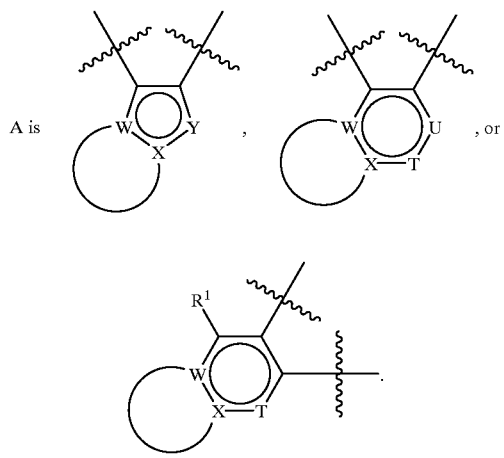

For purposes of illustration only, wherein the bicyclic heteroaryl group A shown is a quinoline, 4-chloro-7-trifluoromethylquinoline-3-carboxylic acid ethyl ester, prepared from the corresponding aniline, is reacted with N-benzyl-p-methoxybenzenesulfonamide, wherein Z is p-methoxybenzene, to provide the requisite N,N-disubstituted sulfonamido-ester which is then converted into the corresponding hydroxamic acid in two steps.

Alternatively, the 4-chloroquinoline carboxylic acid ester could be first reacted with $R^7$—$NH_2$ and the resulting 4-($R^7$-amino)quinoline carboxylic acid ester then reacted with the appropriate Z—$SO_2$—Cl. Hydrolysis of the ester and reaction with hydroxylamine hydro-chloride would then give the invention compound.

Scheme I

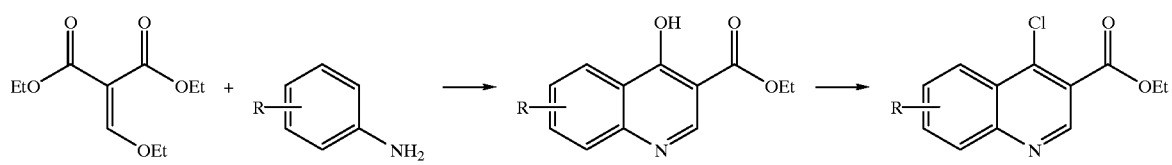

-continued

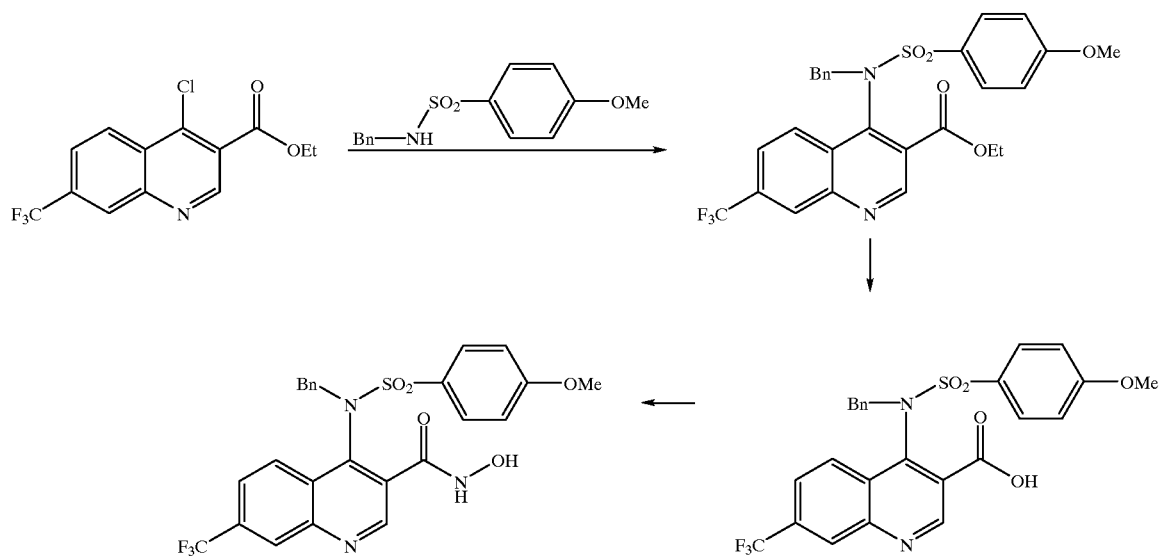

Functionalization of the quinoline ring via a palladium catalyzed Heck coupling between the iodoquinoline and tributylvinyltin is shown in Scheme II. α,β-Unsaturated esters and amides can be coupled to the haloquinoline via Heck reactions. A variety of other trialkyltin reagents are readily available and may be similarly used. Boronic acids, commercially available or readily prepared, may also be coupled to the iodoquinoline using the Suzuki reaction.

Scheme II

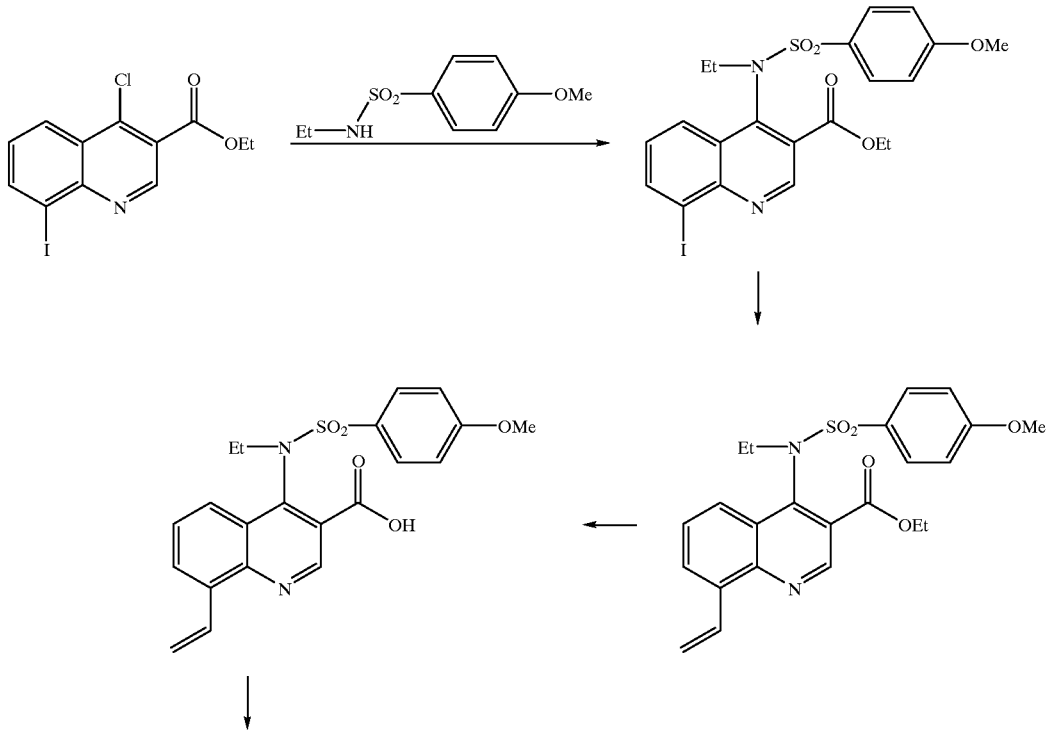

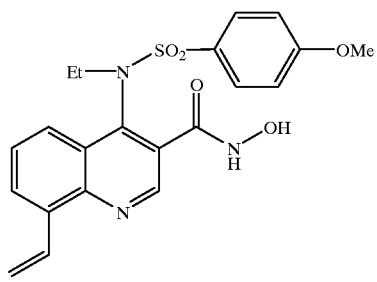

Functionalization of haloquinolines may also be accomplished via palladium catalyzed couplings of alkynes, as illustrated in Scheme III. Hydrogenation of the alkynes accesses the olefins and alkanes as well.

Scheme III

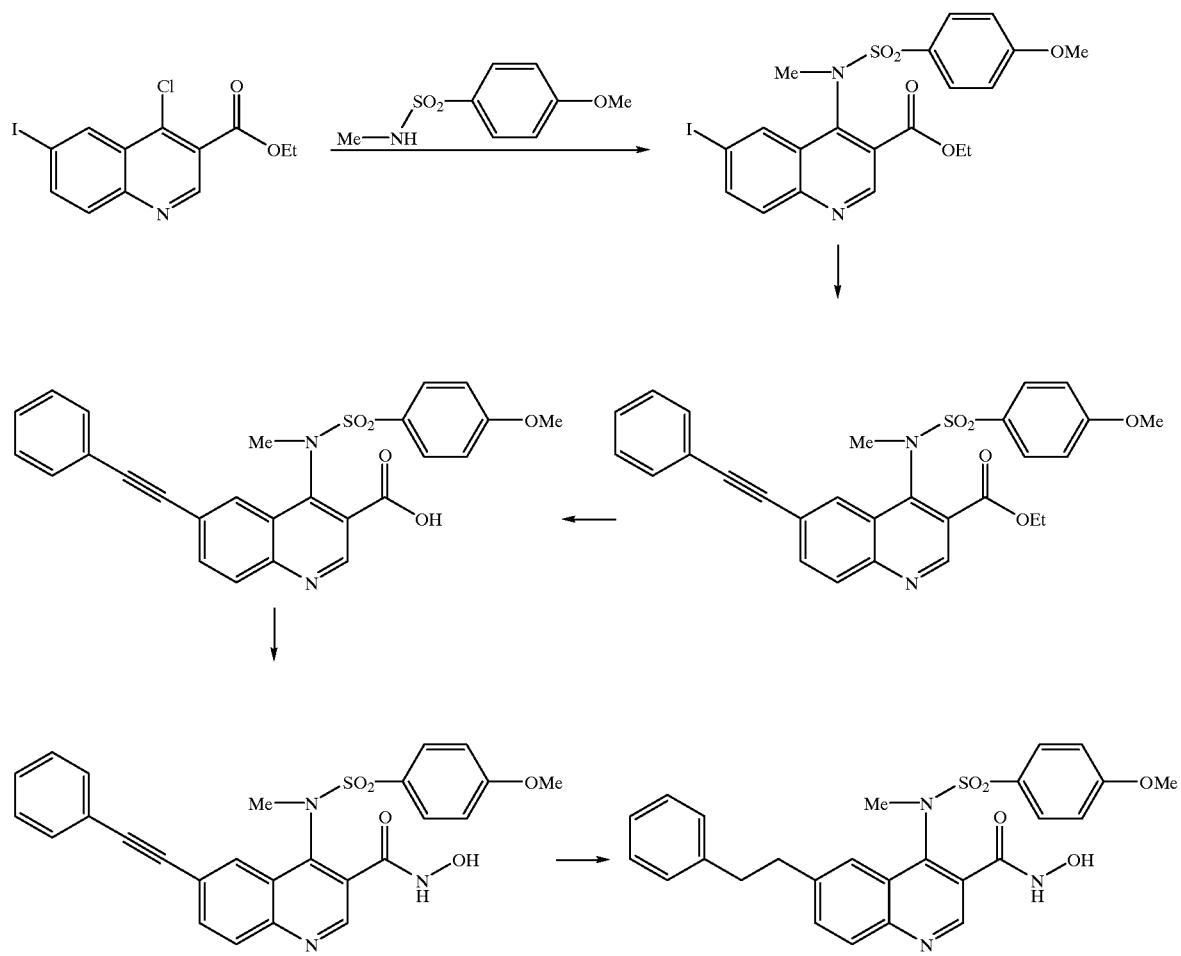

Schemes IV and V illustrate two methods for incorporating amino groups into the substituent attached to the sulfonamide nitrogen of the compounds of the invention. Thus, in Scheme IV the NH-sulfonamide is alkylated with propargyl bromide to provide the propargyl sulfonamide. This alkyne is reacted with paraformaldehyde in the presence of a primary or secondary amine and cuprous chloride to give the propargyl amine which is converted, as before, to the desired hydroxamic acid.

Scheme IV

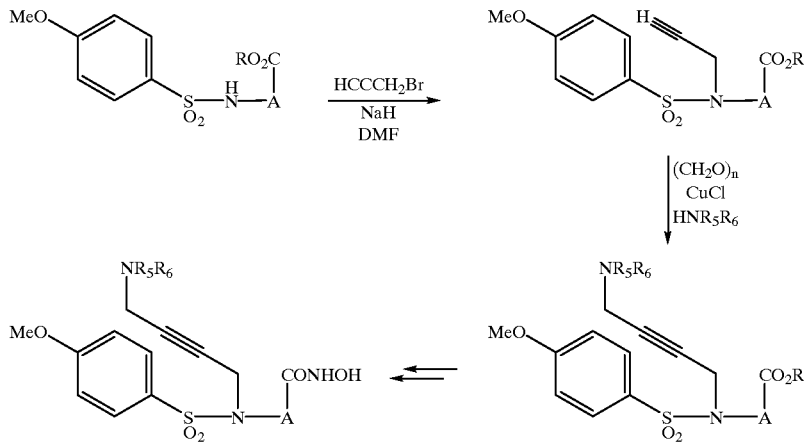

In Scheme V, selective hydrolysis of the ester of the p-carboethoxybenzyl sulfonamide group provides a mono-carboxylic acid. This acid may be converted into an amide (not shown), followed by conversion of the second ester, A—$CO_2$R, into the corresponding hydroxamate, or reduced to the corresponding alcohol with diborane. The alcohol may be converted into the analogous amine via the benzylic bromide, followed by conversion of the the ester, A—$CO_2$R, into the corresponding hydroxamate.

Scheme V

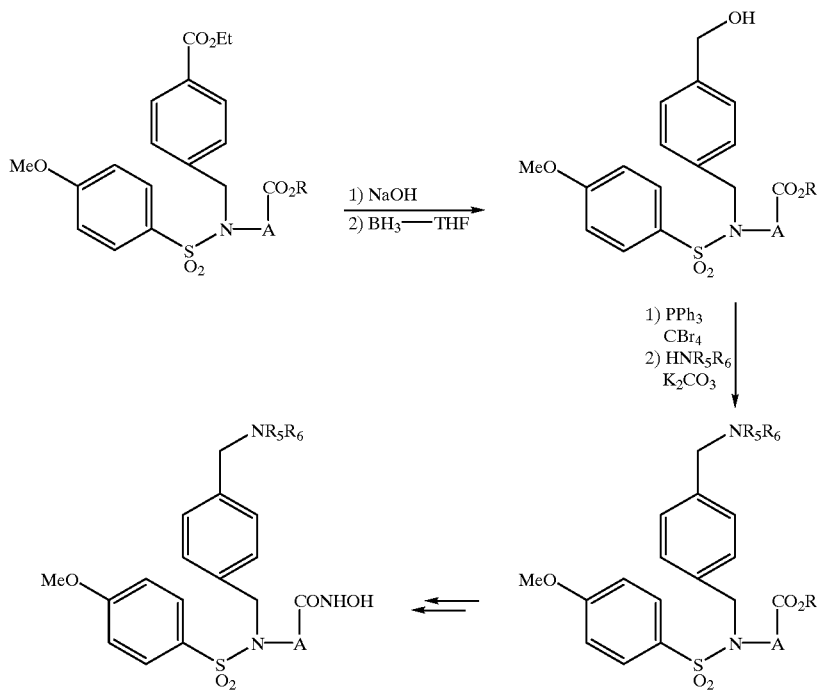

Methods for synthesizing variations of substituents on the sulfonyl aryl group are shown in Schemes VI through VIII. As shown in Scheme VI, biaryl sulfonyl groups are synthesized by Suzuki couplings on a bromo-substituted benzene sulfonamide. The starting bromo-substituted benzene sulfonamide is synthesized from the commercially available bromobenzenesulfonyl chloride and the amino-acid or amino-ester, $H_2N$—A—$CO_2$R, followed by alkylation of the resulting NH-sulfonamide. Alternatively, the bromo aryl sulfonamide is converted into the corresponding boronic acid by the method of Ishiyama, et.al. [J. Org. Chem. (1995), 60, 7508] followed by coupling with an appropriate aryl halide.

Methods for synthesizing sulfonyl aryl ethers are shown in Schemes VII through IX. In Scheme VII biaryl ethers, or aryl heteroaryl ethers, are synthesized starting from the known sulfonyl chlorides (see for example: Zook S E; Dagnino, R; Deason, M E, Bender, S L; Melnick, M J WO 97/20824).

Scheme VI

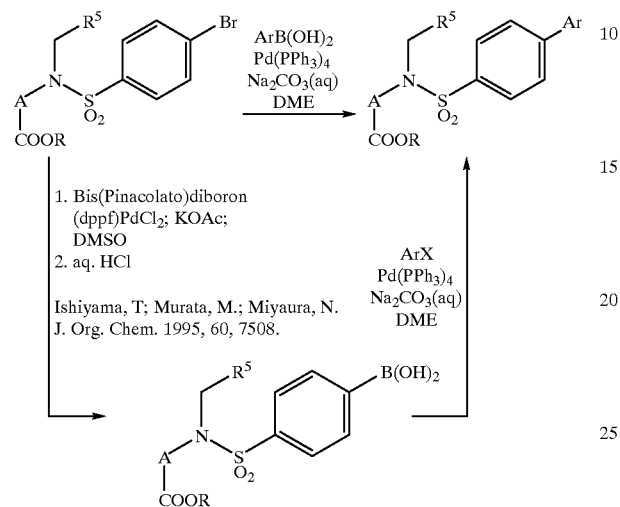

Scheme VII

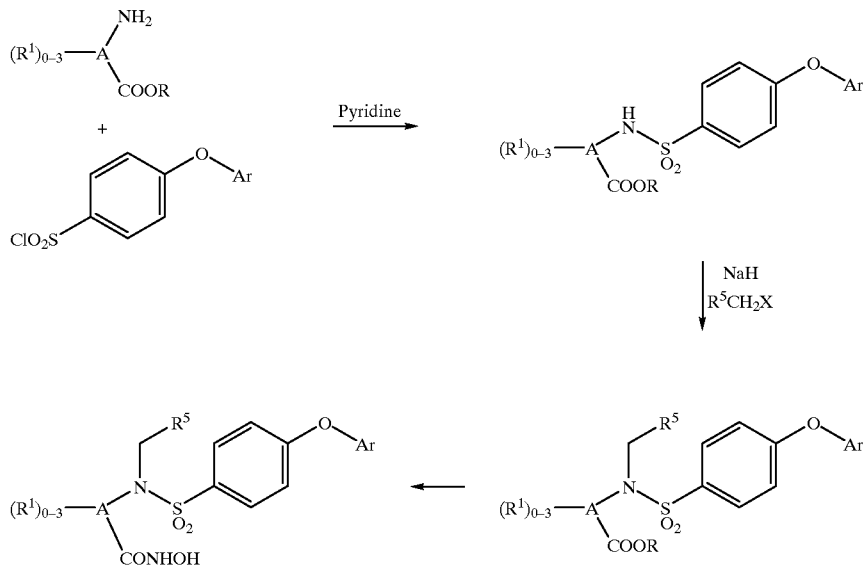

Alternatively, the biaryl ethers may be prepared from the corresponding boronic acids or via the sulfonyl phenols as shown in Scheme VIII.

Scheme VIII

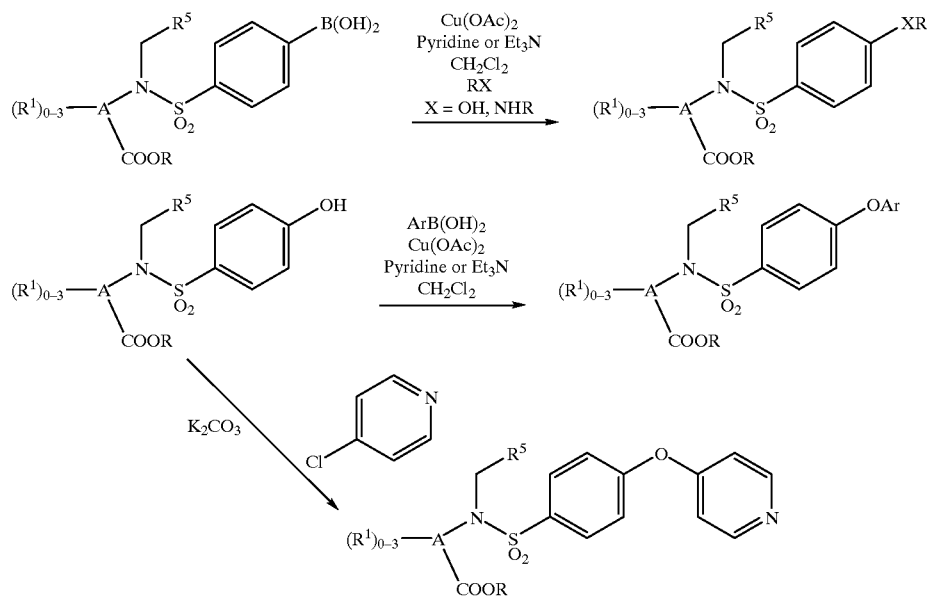

Aryl ethers may also be prepared via displacement of the fluorine from a parafluorobenzene sulfonamide, as shown in Scheme IX. Aryl or alkyl ethers may be prepared in this manner.

Scheme IX

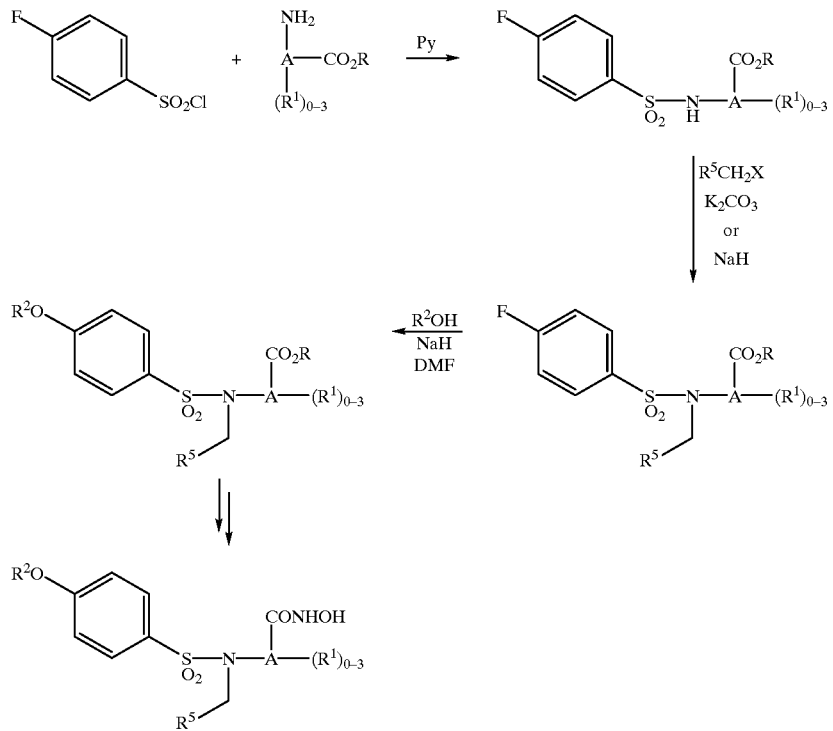

Scheme X illustrates the synthesis of pyrazolopyridines, isoxazolopyridines, and isothiazolopyridines of the invention. Thus, an aminopyrazole, aminoisoxazole or aminoisothiazole is condensed with ethoxymethylene malonate to provide the intermediate, B. This compound is converted into the pyrazolopyridine, isoxazolopyridine, or isothiazolopyridine, C, by heating at 240° C. Compound C is then converted into the chloro-ester, D, via reaction with phosphorus oxychloride. Displacement of the chloro substituent with a sulfonamide then gives compound E. Hydrolysis of the ester and conversion of the carboxylate into the hydroxamate then gives compound G. Salts of the invention compounds can be prepared according to standard procedures.

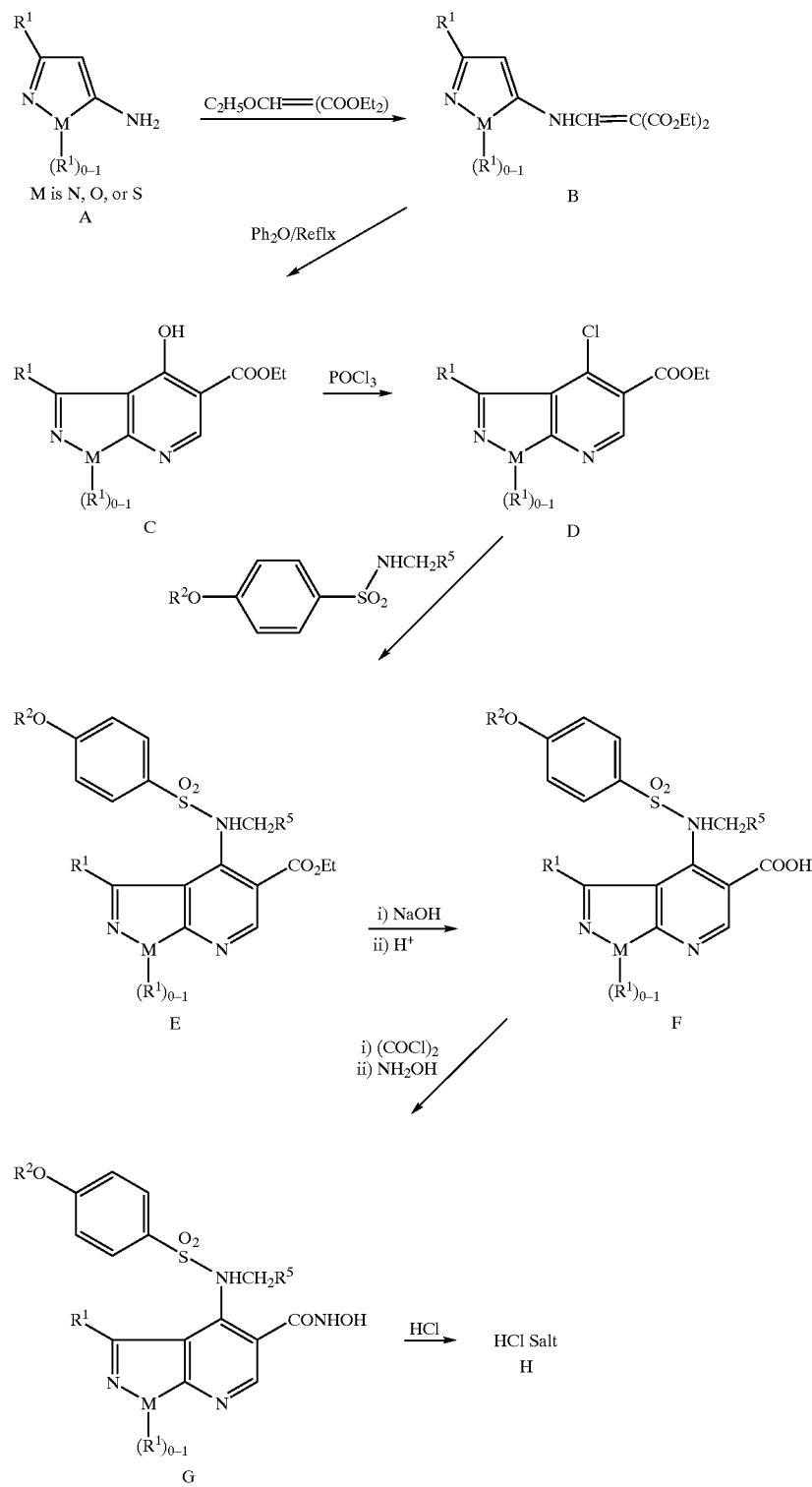

Pyrazolo[1,5-b]pyrimidines of the invention are prepared according to scheme XI using reactions as described for scheme X.

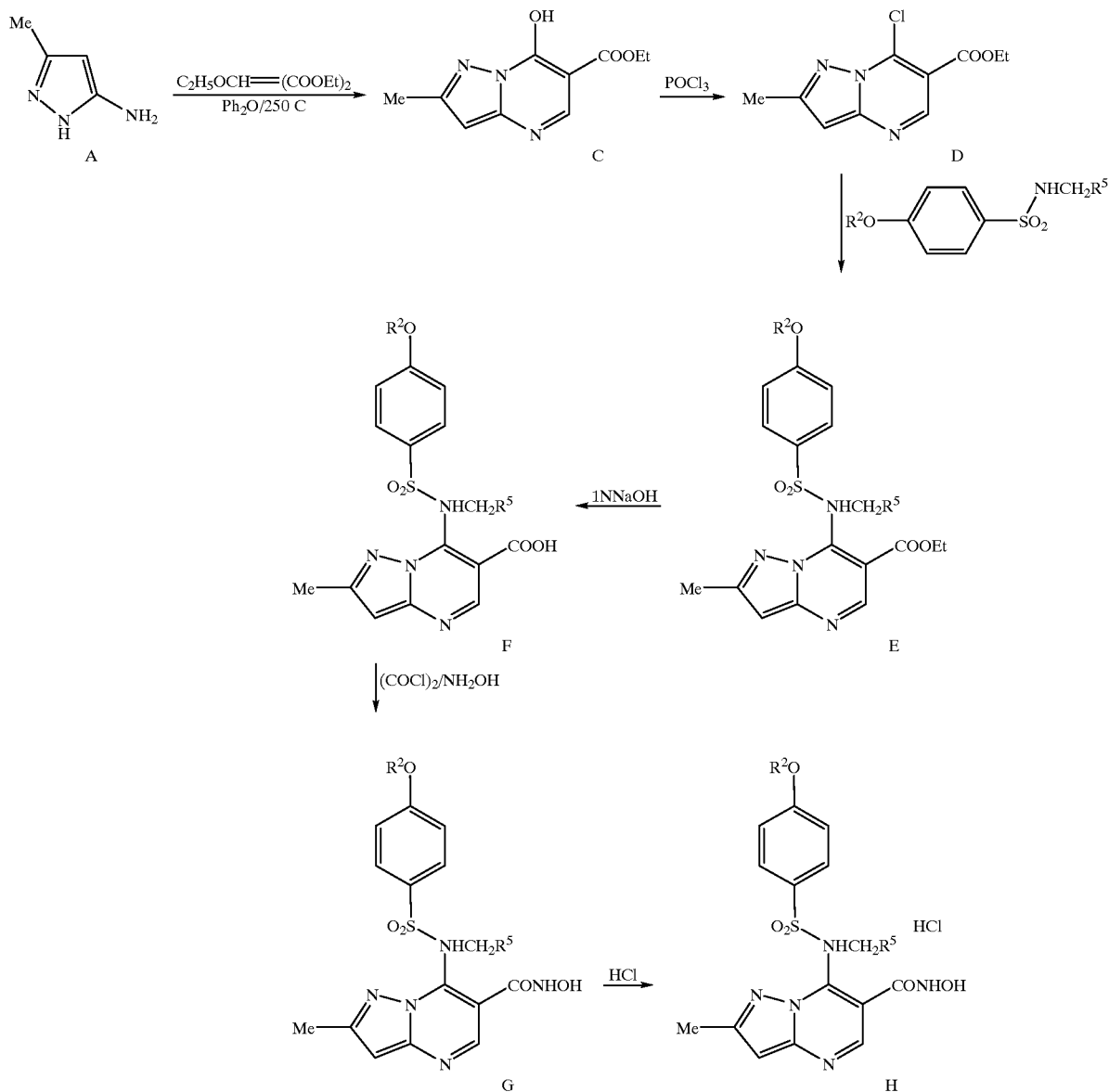

Scheme XI

The following specific examples illustrate the preparation of representative compounds of this invention. The starting materials, intermediates, and reagents are either commercially available or can be readily prepared following standard literature procedures by one skilled in the art of organic synthesis.

EXAMPLE 1

4-[Benzyl-(4-methoxy-benzenesulfonyl)-amino]-7-trifluoromethyl-quinoline-3-carboxylic Acid Ethyl Ester To a solution of 1.85 g (6.67 mmol) of N-benzyl 4-methoxyphenylsulphonamide in 15 mL of DMF was added, in one portion, 0.267 g (6.67 mmol) of 60% sodium hydride and the resulting mixture was stirred at room temperature under nitrogen for 15 min. Ethyl 4-chloro-7-trifluoromethyl-3-quinolinecarboxylate (2.02 g, 6.67 mmol) was then added to the solution in one portion and the resulting mixture was heated at 85° C. for 24 h. The reaction mixture was then cooled to room temperature, poured into a mixture of water (300 mL) and HCl (1N, aqueous, 100 mL) and extracted with ethyl acetate (2×10 mL). The combined organic layers were dried over magnesium sulfate, filtered and concentrated in vacuo. The residue was then chromatographed on silica gel eluting with 15%–50% ethyl acetate/hexane to give 3.11 g (88%) of the desired product. Electrospray Mass Spec 545.1 (M+H).

EXAMPLE 2

4-[Benzyl-(4-methoxy-benzenesulfonyl)-amino]-8-trifluoromethyl-quinoline-3-carboxylic Acid Ethyl Ester In the same manner as described in Example 1, 1.012 g (3.34 mmol) of ethyl 4-chloro-8-trifluoromethyl-3-quinolinecarboxylate provided 1.509 g (83%) of the desired quinoline ester as a white solid. Electrospray Mass Spec 545.1 (M+H).

EXAMPLE 3

4-[Benzyl-(4-methoxy-benzenesulfonyl)-amino]-6-bromo-quinoline-3-carboxylic Acid Ethyl Ester In the same manner as described in Example 1, 0.848 g (2.70 mmol) of ethyl 6-bromo-4-chloro-3-quinolinecarboxylate provided 1.418 g (95%) of the desired quinoline ester as a white solid. Electrospray Mass Spec 557.1 (M+H).

EXAMPLE 4

4-[Benzyl-(4-methoxy-benzenesulfonyl)-amino]-7-bromo-quinoline-3-carboxylic Acid Ethyl Ester In the same manner as described in Example 1, 0.777 g (2.47 mmol) of ethyl 7-bromo-4-chloro-3-quinolinecarboxylate provided 1.169 g (85%) of the desired quinoline ester as a white solid. Electrospray Mass Spec 557.1 (M+H).

EXAMPLE 5

4-[Benzyl-(4-methoxy-benzenesulfonyl)-amino]-6-trifluoromethyl-quinoline-3-carboxylic Acid Ethyl Ester In the same manner as described in Example 1, 1.216 g (4.02 mmol) of ethyl 4-chloro-6-trifluoromethyl-3-quinolinecarboxylate provided 2.171 g (99%) of the desired quinoline ester as a white solid. Electrospray Mass Spec 545.0 (M+H).

EXAMPLE 6

4-[Benzyl-(4-methoxy-benzenesulfonyl)-amino]-7-trifluoromethyl-quinoline-3-carboxylic Acid To a solution of 1.065 g (2.00 mmol) of the product from Example 1 in 4 mL of methanol/THF (1:1) was added 2 mL of 1N sodium hydroxide solution and the resulting mixture was stirred at 25° C. for 18 h. The reaction was then acidified with 1N HCl and extracted with ethyl acetate (200 mL). The organic layer was washed with water and brine, dried over $MgSO_4$, filtered and concentrated in vacuo. The resulting residue was triturated with ethyl acetate/hexane (1:9) and filtered to provide 828 mg (82%) of the desired carboxylic acid as a white solid. Electrospray Mass Spec 517.1 (M+H)

EXAMPLE 7

4-[Benzyl-(4-methoxy-benzenesulfonyl)-amino]-8-trifluoromethyl-quinoline-3-carboxylic Acid In the same manner as described in Example 6, 1.255 g (2.64 mmol) of the product from Example 2 provided 0.988 g (83%) of the desired quinoline acid as a white solid. Electrospray Mass Spec 517.1 (M+H).

EXAMPLE 8

4-[Benzyl-(4-methoxy-benzenesulfonyl)-amino]-6-bromo-quinoline-3-carboxylic Acid In the same manner as described in Example 6, 1.198 g (2.16 mmol) of the product from Example 3 provided 0.921 g (81%) of the desired quinoline acid as a white solid. Electrospray Mass Spec 529.0 (M+H).

EXAMPLE 9

4-[Benzyl-(4-methoxy-benzenesulfonyl)-amino]-7-bromo-quinoline-3-carboxylic Acid In the same manner as described in Example 6, 0.969 g (1.74 mmol) of the product from Example 4 provided 0.804 g (87%) of the desired quinoline acid as a white solid. Electrospray Mass Spec 529.0 (M+H).

EXAMPLE 10

4-[Benzyl-(4-methoxy-benzenesulfonyl)-amino]-6-trifluoromethyl-quinoline-3-carboxylic Acid In the same manner as described in Example 6, 2.043 g (3.75 mmol) of the product from Example 5 provided 1.82 g (88%) of the desired quinoline acid as a white solid. Electrospray Mass Spec 515.0 (M–H).

EXAMPLE 11

4-[Benzyl-(4-methoxy-benzenesulfonyl)-amino]-7-trifluoromethyl-quinoline-3-carboxylic acid hydroxyamide To a solution of 0.636 g (1.26 mmol) of the product from Example 6 in 12.5 mL of dichloromethane was added 0.05 mL of DMF followed by 1.26 mL (2.52 mmol) of 2 M oxalyl chloride and the resulting reaction mixture was stirred at room temperature for 1 h.

In a separate flask, 2.6 mL (19 mmol) of triethylamine was added to a 0° C. mixture of 350 mg (13 mmol) of hydroxylamine hydrochloride in 14 mL of THF and 3.5 mL of water. After this mixture had been stirred for 15 min at 0° C., the acid chloride solution was added to it in one portion and the resulting solution was allowed to warm to room temperature and stirred for another 4 h. Water was then added to the reaction flask and 0.488 g (75%) product was collected via filtration. Electrospray Mass Spec 532.1 (M+H)

EXAMPLE 12

4-[Benzyl-(4-methoxy-benzenesulfonyl)-amino]-8-trifluoromethyl-quinoline-3-carboxylic acid hydroxyamide In the same manner as described in Example 11, 0.444 g (3.75 mmol) of the product from Example 7 provided 0.143 g (31%) of the desired quinoline hydroxamic acid as a cream colored solid. Electrospray Mass Spec 532.1 (M+H).

EXAMPLE 13

4-[Benzyl-(4-methoxy-benzenesulfonyl)-amino]-6-bromo-quinoline-3-carboxylic Acid Hydroxyamide In the same manner as described in Example 11, 0.527 g (1.00 mmol) of the product from Example 8 provided 0.367 g (68%) of the desired quinoline hydroxamic acid as a off-white solid. Electrospray Mass Spec 541.9 (M+H).

EXAMPLE 14

4-[Benzyl-(4-methoxy-benzenesulfonyl)-amino]-7-bromo-quinoline-3-carboxylic Acid Hydroxyamide In the same manner as described in Example 11, 0.527 g (1.00 mmol) of the product from Example 9 provided 0.280 g (52%) of the desired quinoline hydroxamic acid as a white solid. Electrospray Mass Spec 541.9 (M+H).

EXAMPLE 15

4-[Benzyl-(4-methoxy-benzenesulfonyl)-amino]-6-trifluoromethyl-quinoline-3-carboxylic Acid Hydroxyamide In the same manner as described in Example 11, 0.527 g (1.06 mmol) of the product from Example 10 provided 0.435 g (77%) of the desired quinoline hydroxamic acid as a cream colored solid. Electrospray Mass Spec 532.1 (M+H).

EXAMPLE 16

4-[(4-Methoxybenzenesulfonyl)-pyridin-3-ylmethylamino]-7-trifluoromethyl-quinoline-3-carboxylic Acid Hydroxyamide Following the procedure of example 1 and substituting N-(3-pyridinylmethyl)-4-methoxybenzenesulfonamide for N-benzyl-4-methoxybenzenesulfonamide, the intermediate 4-[(4-methoxybenzenesulfonyl)-pyridin-3-ylmethylamino]-7-trifluoromethyl-quinoline-3-carboxylic acid ethyl ester is obtained. Following the procedures of example 6 and 11, the title product is obtained. Electrospray Mass Spec 533.0 (M+H).

EXAMPLE 17

4-[Benzyl-(4-methoxybenzenesulfonyl)-amino]-8-t-butyl-quinoline-3-carboxylic Acid Hydroxyamide In the same manner as described in Example 1, 1.167 g (4.00 mmol) of ethyl 4-chloro-8-butyl-3-quinolinecarboxylate provided 1.413 g (66%) of the desired quinoline ester as a white solid. Electrospray Mass Spec 533.3 (M+H).

In the same manner as described in Example 6, 1.065 g (2.00 mmol) of the ester provided 0.478 g (47%) of the desired quinoline acid as a white solid. Electrospray Mass Spec 503.3 (M−H).

Following the procedures of example, the title compound is obtained from the carboxylic acid. Electrospray Mass Spec. 520.3 (M+H).

EXAMPLE 18

4-[Benzyl-(4-methoxybenzenesulfonyl)-amino]-8-methyl-quinoline-3-carboxylic Acid Hydroxyamide In the same manner as described in Example 1, 1.00 g (4.00 mmol) of ethyl 4-chloro-8-methyl-3-quinolinecarboxylate provided 0.531 g (27%) of the desired quinoline ester as a white solid. Electrospray Mass Spec 491.3 (M+H).

In the same manner as described in Example 6, 0.470 g (0.851 mmol) of the ester provided 0.160 g (41%) of the desired quinoline acid as a white solid. Electrospray Mass Spec 461.3 (M−H).

Following the procedure of example 11, the title compound is obtained from the carboxylic acid. Electrospray Mass Spec. 478.3 (M+H).

EXAMPLE 19

4-[Benzyl-(4-methoxybenzenesulfonyl)-amino]-8-ethyl-quinoline-3-carboxylic Acid Hydroxyamide In the same manner as described in Example 1, 1.055 g (4.00 mmol) of ethyl 4-chloro-8-ethyl-3-quinolinecarboxylate provided 0.670 g (33%) of the desired quinoline ester as a white solid. Electrospray Mass Spec 505.3 (M+H).

In the same manner as described in Example 6, 0.615 g (1.22 mmol) of the product from Example 7 provided 0.353 g (60%) of the desired quinoline acid as a white solid. Electrospray Mass Spec 475.3 (M−H).

Following the procedure of example 11, the title compound is obtained from the carboxylic acid. Electrospray Mass Spec. 492.3 (M+H).

EXAMPLE 20

4-[Benzyl-(4-methoxybenzenesulfonyl)-amino]-8-(1-methylethyl)-quinoline-3-carboxylic Acid Hydroxyamide In the same manner as described in Example 1, 1.111 g (4.00 mmol) of ethyl 4-chloro-8-isopropyl-3-quinolinecarboxylate provided 0.754 g (36%) of the desired quinoline ester as a white solid. Electrospray Mass Spec 519.3 (M+H).

In the same manner as described in Example 6, 0.686 g (0.127 mmol) of the ester provided 0.532 g (82%) of the desired quinoline acid as a white solid. Electrospray Mass Spec 489.2 (M−H).

In the same manner as described in Example 11, 0.440 g (0.897 mmol) of the hydroxamic acid provided 0.270 g (60%) of the desired quinoline hydroxamic acid. Electrospray Mass Spec. 506.3 (M+H).

EXAMPLE 21

4-[Ethyl-(4-methoxy-benzenesulfonyl)-amino]-8-iodo-quinoline-3-carboxylic Acid Ethyl Ester In the same manner as described in Example 1 and substituting N-ethyl-4-methoxybenzenesulfonamide for N-benzyl-4-methoxybenzenesulfonamide, 1.076 g (5.00 mmol) of ethyl 8-iodo-4-chloro-3-quinolinecarboxylate provided 2.438 g (4.51 mmol, 90%) of the desired quinoline ester as a white solid. Electrospray Mass Spec 541.0 (M+H).

EXAMPLE 22

4-[Ethyl-(4-methoxy-benzenesulfonyl)-amino]-8-vinyl-quinoline-3-carboxylic Acid Ethyl Ester The product from example 21 (2.438 g, 4.51 mmol) in 150 mL DMF was added tributylvinyltin (1.43 g, 4.51 mmol), tetrakis(triphenylphosphine)palladium(0) (520 mg, 10%), cuprious iodide (171 mg, 20%), and 5 mL triethylamine. The mixture was stirred under N2 and heated at 85° C. for 18 hours. The it was poured into a mixture (1:1) of 400 mL saturated sodium bicarbonate and saturated ammonium chloride and extracted with ethyl acetate (2×200 mL). The combined organic layers were dried over magnesium sulfate, filtered and concentrated on a rotary evaporator. The residue was column chromatographed using 300 mL silica gel and gradient elution with hexane/ethyl acetate (100–0%). This provided 1.706 g (3.88 mmol, 86%) of the desired quinoline ester. Electrospray Mass Spec 441.1 (M+H).

EXAMPLE 23

4-[Methyl-(4-methoxy-benzenesulfonyl)-amino]-6-phenylethynyl-quinoline-3-carboxylic acid ethyl ester Combining the procedures of examples 1 and 22, and substituting phenylacetylene for vinyltin, N-ethyl-4-methoxybenzenesulfonamide for N-benzyl-4-methoxybenzenesulfonamide, the intermediate 4-[ethyl-(4-methoxy-benzenesulfonyl)-amino]-6-phenylethynyl-quinoline-3-carboxylic acid ethyl ester is obtained from ethyl-4-chloro-3-quinolinecarboxylate. Electrospray Mass Spec 515.3 (M+H).

EXAMPLE 24

4-[Ethyl-(4-methoxy-benzenesulfonyl)-amino]-8-vinyl-quinoline-3-carboxylic Acid In the same manner as described in Example 6, 1.593 g (3.62 mmol) of the product from Example 22 provided 1.333 g (89%) of the desired quinoline acid as a white solid. Electrospray Mass Spec 411.1 (M−H).

EXAMPLE 25

4-[Methyl-(4-methoxy-benzenesulfonyl)-amino]-6-phenylethynyl-quinoline-3-carboxylic Acid In the same manner as described in Example 6, the title compound was synthesized from the product of example 23. Electrospray Mass Spec 485.3 (M−H).

EXAMPLE 26

4-[Benzyl-(4-methoxy-benzenesulfonyl)-amino]-6-nitro-quinoline-3-carboxylic Acid In the same manner as described in Example 1 and 6, 5613 g (20.0 mmol) ethyl 4-chloro-6-nitro-3-quinolinecarboxylate provided 2.676 g (27% for two steps) of the title compound as a white solid. Electrospray Mass Spec 492.3 (M−H).

EXAMPLE 27

4-[Methyl-(4-methoxy-benzenesulfonyl)-amino]-8-bromo-quinoline-3-carboxylic Acid Combining the procedures of example 1 and 6, and substituting N-methyl-4-methoxybenzenesulfonamide for N-benzyl-4-methoxybenzenesulfonamide, the intermediate 8-bromo-4-[methyl-(4-methoxy-benzenesulfonyl)-amino]-quinoline-3-carboxylic acid is obtained. Electrospray Mass Spec 449.2 (M−H).

EXAMPLE 28

4-{Methyl-(4-(pyridin-4-yloxy)-benzenesulfonyl]-amino}-6-iodo-quinoline-3-carboxylic acid Combining the procedures of example 1 and 6, and substituting N-methyl-4-(pyridin-4-yloxy)-benzenesulfonamide the intermediate 6-iodo-4-{methyl-(4-(pyridin-4-yloxy)-benzenesulfonyl]-amino}-quinoline-3-carboxylic acid is obtained from ethyl 6-iodo-4-chloro-3-quinolinecarboxylate. Electrospray Mass Spec 559.9 (M−H).

EXAMPLE 29

4-[Ethyl-(4-methoxy-benzenesulfonyl)-amino]-8-vinyl-quinoline-3-carboxylic Acid Hydroxyamide In the same manner as described in Example 11, 0.484 g (1.17 mmol) of the product from Example 24 provided 0.360 g (72%) of the desired quinoline hydroxamic acid. Electrospray Mass Spec. 428.0 (M+H).

EXAMPLE 30

4-[Benzyl-(4-methoxy-benzenesulfonyl)-amino]-6-nitro-quinoline-3-carboxylic Acid Hydroxyamide In the same manner as described in Example 11, 0.825 g (1.67 mmol) of the product from Example 26 provided 0.227 g (0.446 mmol, 26%) of the desired quinoline hydroxamic acid. Electrospray Mass Spec. 509.0 (M+H).

EXAMPLE 31

4-[Methyl-(4-methoxy-benzenesulfonyl)-amino]-8-bromo-quinoline-3-carboxylic Acid Hydroxyamide In the same manner as described in Example 11, 0.664 g (1.47 mmol) of the product from Example 27 provided 0.145 g (0.311 mmol, 21%) of the desired quinoline hydroxamic acid. Electrospray Mass Spec. 468.0 (M+H).

EXAMPLE 32

4-{Methyl-[4-(pyridin-4-yloxy)-benzenesulfonyl]-amino}-6-iodo-quinoline-3-carboxylic Acid Hydroxyamide To a 0° C. solution of of 4.5 mL oxalyl chloride (0.90 mmol, 2M in dichloromethane) was added dropwise 0.69 mL of DMF. The resulting solid was kept at 0° C. for another 15 minutes and followed by addition of 2.50 g (4.46 mmol) of the product from Example 28 in 50 mL DMF. The mixture was stirred for 1 hour at room temperature and then kept at 0° C. for an additional 15 minutes. An aqueous solution of hydroxylamine (5 mL, 50%) was then added all at once to the above solution and the mixture was stirred at room temperature for 3 hours. The mixture was next poured into 300 mL water and extracted with dichloromethane (4×100 mL). The combined organic layers were washed with brine (300 mL) and dried over magnesium sulfate. After filtration and concentration on a rotary evaporator the residue was column chromatographed using gradient methanol in ethyl acetate (20~100%) and it provided 1.36 g (2.36 mmol, 53%) of the desired quinoline hydroxamic acid. Electrospray Mass Spec. 576.9 (M+H).

EXAMPLE 33

4-{Methyl-(4-(pyridin-4-yloxy)-benzenesulfonyl]-amino}-6-iodo-quinoline-3-carboxylic Acid Hydroxyamide Hydrochloride The product from example 32 (0.952 g, 1.65 mmol) was dissolved in 100 mL methanol in a Parr reactor. Degussa catalyst (10% Pd—C, 200 mg) was next added under N2. The mixture was then hydrogenated (35 psi) for one hour at room temperature. The mixture was then filtered through a pad of celite and concentrated on a rotary evaporator. The residue was chromatographed with methanol and ethyl acetate (5~35%). The product obtained was next dissolved in methanol and anhydrous hydrochloride was bubbled into the solution for 5 minutes. Removal of the solvent through rotary evaporation and vacuum pump gave 0.707 g (1.45 mmol, 88%) product. Electrospray Mass Spec. 450.9 (M+H).

EXAMPLE 34

4-[Ethyl-(4-methoxy-benzenesulfonyl)-amino]-6-phenylethynyl-quinoline-3-carboxylic Acid Hydroxyamide In the same manner as described in Example 11, 2.432 g (5.00 mmol) of the product from Example 25 provided 2.159 g (86%) of the desired quinoline hydroxamic acid. Electrospray Mass Spec. 502.1 (M+H).

EXAMPLE 35

4-[Methyl-(4-methoxy-benzenesulfonyl)-amino]-6-phenylethyl-quinoline-3-carboxylic Acid Hydroxyamide The product from example 34 (0.82 g, 1.64 mmol) was dissolved in 50 mL methanol in a Parr reactor. Degussa Catalyst (10% Pd—C, 200 mg) was next added under N2. The mixture was hydrogenated (45 psi) for one hour at room temperature. The mixture was then filtered through a pad of celite and concentrated on a rotary evaporator. This gave 0.76 g (1.50 mmol, 92%) product. Electrospray Mass Spec. 506.0 (M+H).

EXAMPLE 36

4-[(4-Methoxy-benzenesulfonyl)-pyridin-3-ylmethyl-amino]-8-methoxy-quinoline-3-carboxylic Acid Hydroxyamide Following the procedure of Example 16 and starting with ethyl 4-chloro-8-methoxy-3-quinolinecarboxylate the title compound was obtained as a yellow powder. Electrospray Mass Spec. 495.3 (M+H).

EXAMPLE 37

4-[(4-Methoxy-benzenesulfonyl)-pyridin-3-ylmethyl-amino]-8-bromo-quinoline-3-carboxylic Acid Hydroxyamide Following the procedure of Example 16 and starting with ethyl 4-chloro-8-bromo-3-quinolinecarboxylate the title compound was obtained as a white powder. Electrospray Mass Spec. 543.2 (M+H).

EXAMPLE 38

4-[(4-methoxy-benzenesulfonyl)-pyridin-3-ylmethyl amino]-8-Benzyl-quinoline-3-carboxylic Acid Hydroxyamide Following the procedure of Example 16 and starting with ethyl 4-chloro-8-benzyl-3-quinolinecarboxylate the title compound was obtained as a beige powder. Electrospray Mass Spec. 555.4 (M+H).

EXAMPLE 39

4-[(4-Methoxy-benzenesulfonyl)-pyridin-3-ylmethyl-amino]-8-iodo-quinoline-3-carboxylic Acid Hydroxyamide Following the procedure of Example 16 and starting with ethyl 4-chloro-8-iodo-3-quinolinecarboxylate the title compound was obtained as a yellow powder. Electrospray Mass Spec. 590.8 (M+H).

EXAMPLE 40

4-[(4-Methoxy-benzenesulfonyl)-pyridin-3-ylmethyl-amino]-8-phenyl-quinoline-3-carboxylic Acid Hydroxyamide Following the procedure of Example 16 and starting with ethyl 4-chloro-8-phenyl-3-quinolinecarboxylate the title compound was obtained as a beige powder. Electrospray Mass Spec. 541.4 (M+H).

EXAMPLE 41

4-[(4-Methoxy-benzenesulfonyl)-pyridin-3-ylmethyl-amino]-8-thiophen-2-yl-quinoline-3-carboxylic Acid Hydroxyamide Combining the procedures of Examples 22, 6 and 11 and starting with 4-[(4-methoxy-benzenesulfonyl)-pyridin-3-ylmethyl-amino]-8-bromo-quinoline-3-carboxylic acid ethyl ester and 2-tributylstannylthiophene the title compound was obtained as a yellow powder. Electrospray Mass Spec. 545.0 (M+H).

EXAMPLE 42

4-[(Biphenyl-4-sulfonyl)-pyridin-3-ylmethyl-amino]-7-trifluoromethyl-quinoline-3-carboxylic Acid Hydroxyamide Following the procedure of Example 1 and substituting N-(3-pyridinylmethyl)-4-bromobenzenesulfonamide for N-benzyl-4-methoxybenzenesulfonamide, the intermediate 4-[(4-bromobenzenesulfonyl)-pyridin-3-ylmethylamino]-7-trifluoromethyl-quinoline-3-carboxylic acid ethyl ester is obtained.

To 8.5 mL of degassed ethylene glycol dimethyl ether, was added 500 mg (0.85 mmol) of the ester, 110 mg (0.93 mmol) of phenylboronic acid, 80 mg (0.07 mmol) of tetrakis(triphenylphosphine)palladium and 1.1 ml (2.2 mmol) of 2M aqueous $Na_2CO_3$ and the mixture ws heated to reflux under nitrogen for 36 hr. The reaction was cooled to room temperature, diluted with ethyl acetate, washed with water and brine, dried over $MgSO_4$, filtered and concentrated in vacuo to give 4-[(biphenyl-4-sulfonyl)-pyridin-3-ylmethyl-amino]-7-trifluoromethyl-quinoline-3-carboxylic acid ethyl ester.

This ester was converted to the title compound (off-white powder) as described in Examples 6 and 11. Electrospray Mass Spec. 579.1 (M+H).

EXAMPLE 43

4-[(Octane-1-sulfonyl)-pyridin-3-ylmethyl-amino]-7-trifluoromethyl-quinoline-3-carboxylic Acid Hydroxyamide Combining the procedures of Examples 1, 6 and 11 and substituting N-(3-pyridinylmethyl)-octanesulfonamide for N-benzyl-4-methoxybenzenesulfonamide the title compound was obtained as a yellow solid. Electrospray Mass Spec. 539.5 (M+H).

EXAMPLE 44

4-[Pyridin-3-ylmethyl-(toluene-4-sulfonyl)-amino]-7-trifluoromethyl-quinoline-3-carboxylic Acid Hydroxyamide Combining the procedures of Examples 1, 6 and 11 and substituting N-(3-pyridinylmethyl)-toluenesulfonamide for N-benzyl-4-methoxybenzenesulfonamide the title compound was obtained as a white powder. Electrospray Mass Spec. 517.1 (M+H).

EXAMPLE 45

Diethyl{[(1-phenyl-5-pyrazolyl) amino] methylene}malonate

A mixture of 15.9 g. (0.10 mole) of 1-phenyl-5-aminopyrazole and 21.6 g. (0.10 mole) of diethyl ethoxymethylenemalonate was heated at 115–120° in an oil bath for 2 hours. After cooling, the crystalline mass was recrystallized from hot hexane containing 1% of ethanol. Cooling to room temperature and filtering gave 24.8 g. (75%) of off-white crystals, m.p. 96–97° C.

EXAMPLE 46

Ethyl 4-hydroxy-1-phenyl-1H-pyrazolo[3,4-b] pyridine-5-carboxylate

A mixture of 18.1 g. (0.055 mole) of diethyl{[(1-phenyl-5-pyrazolyl)amino]methylene}malonate and 150 ml of diethyl phthalate was heated at 240–250° for 1 hour. The mixture was chilled and diluted with hexane. Chilling and filtering gave crystals which were washed with hexane and with hexane-ethanol (1:1) to give 11 g. (70%) of off white crystals m.p. 149–150° C. From a similar small scale run 1.75 g. was recrystallized from 110 ml. of ethanol to give 1.58 g. of off white crystals, m.p. 149–150° C.

EXAMPLE 47

Ethyl 4-chloro-1-phenyl-1H-pyrazolo[3,4-b] pyridine-5-carboxylate

A mixture of 5.76 g (20.33 mmol) of ethyl 4-hydroxy-1-phenyl-1H-pyrazolo[3,4-b]pyridine-5-carboxylate and 15.58 g of phosphorus oxychloride was refluxed 1.5 hr, chilled and poured slowly onto crushed ice. The mixture was filtered and the solid washed with ice-water and dried to give 6.0 g of solid, m.p. 89–91° C.

EXAMPLE 48

Ethyl 4-chloro-1,3-dimethyl-1H-pyrazolo[3,4-b] pyridine-5-carboxylate

Following the procedures of Examples 45, 46 and 47, starting from 1,3-dimethyl-5-aminopyrazole, the chloro-ester is prepared. m.p. 89–90° C.

EXAMPLE 49

Ethyl 4-[benzyl-(4-methoxybenzenesulfonyl) amino]-1,3-dimethyl-1H-pyrazolo[3,4-b]pyridine-5-carboxylate To a solution of 1.16 g (4.2 mmol) of benzyl-(4-methoxybenzenesulfonyl)amine in 6 ml of anhydrous 1-methyl-2-pyrrolidinone was added 0.168 g (4.2 mmol) of sodium hydride (60% in oil) and the mixture stirred at room temperature until gas evolution ceased. The preceding mixture was added to mixture of 1.01 g (4=mol) of ethyl 4-chloro-1,3-dimethylpyrazolo[3,4-b]pyridine-5-carboxylate in 2 ml of 1-methyl-2-pyrrolidinone.

The mixture was heated in an oil bath at 50° C. overnight and then was heated in an oil bath at 100° C. for 1.5 days. The mixture was poured into 800 ml of water and extracted with ethyl acetate. The extract was washed with water, 2N citric acid, water, brine and dried ($Na_2SO_4$). The solvent was removed and the residue chromatographed on silica gel with hexane-ethyl acetate (2:1) as eluent to give 0.64 g of product as a solid, mp 170–172°. From a larger scale run of 5.07 g (0.02 mmol) of ethyl 4-chloro-1,3-dimethylpyrazolo[3,4-b] pyridine-5-carboxylate and 8.0 g (0.0289 mmol) of benzyl-(4-methoxybenzenesulfonyl) amine (as sodium anion) in 30 ml of 1-methyl-2-pyrrolidinone heated at 90° C. for 3 days there was obtained 3.65 g of product.

EXAMPLE 50

4-[Benzyl-(4-methoxybenzenesulfonyl)amino]-1,3-dimethyl-1H-pyrazolo[3,4-b]pyridine-5-carboxylic Acid A mixture of 0.48 g (0.97 mmol) of ethyl 4-[benzyl-(4-methoxybenzenesulfonyl) amino]-1,3-dimethyl-1H-pyrazolo[3,4-b]pyridine-5-carboxylate and 0.29 ml of 10N NaOH in 4 ml of tetrahydrofuran-methanol (1:1) was heated in an oil bath at 70° C. for 2 hours and the solvent removed under vacuum. The residue was dissolved in 20 ml of $H_2O$ and the solution extracted with 10 ml of diethyl ether. To the aqueous layer was added 2N citric acid (pH 4–5) and the precipitated solid filtered and washed with $H_2O$ to give a white solid which was dried under vacuum overnight to give crystals, mp 165–167° C.

EXAMPLE 51

4-[Benzyl-(4-methoxybenzenesulfonyl)amino]-1,3-dimethyl-1H-pyrazolo[3,4-b]pyridine-5-carboxylic acid, potassium salt.

A mixture of 3.60 g (7.28 mmol) of ethyl 4-[benzyl-(4-methoxybenzenesulfonyl)amino]-1,3-dimethyl-1H-pyrazolo[3,4-b]pyridine-5-carboxylate and 0.44 g (7.84 mmol) of potassium hydroxide (pellet) in 15 ml of methanol-water (1:1) was refluxed overnight. An additional 40 mg of potassium hydroxide was added and the mixture refluxed for 4 hours (all the solid dissolved). The solvent was removed under vacuum and toluene added and removed under vacuum. The residue was triturated with ethyl acetate, filtered and the solid washed with ethyl acetate to give 3.8 g of product as a white solid.

EXAMPLE 52

4-[Benzyl-(4-methoxybenzenesulfonyl)amino]-1,3-dimethyl-1H-pyrazolo[3,4-b]pyridine-5-carboxylic acid, hydroxyamide To a chilled solution of 1 ml (2 mmol) of oxalyl chloride in 8 ml of $CH_2Cl_2$ was added dropwise 0.154 ml (2 mmol) of N, N-dimethylformamide and the solution stirred 15 min. To the preceding chilled solution was added 0.504 g (1 mmol) of 4-[benzyl-(4-methoxybenzenesulfonyl) amino]-1,3-dimethyl-1H-pyrazolo[3,4-b]pyridine-5-carboxylic acid, potassium salt and the mixture stirred under nitrogen for 2 hrs at room temperature (solution A). A solution of 0.278 g (4 mmol) of hydroxylamine hydrochloride and 0.834 ml (6 mmol) of triethylamine in 5 ml of $H_2O$-tetrahydrofuran (1:4) was chilled at in an ice bath for 20 min. and to this solution was added dropwise the chilled solution of A. The mixture was allowed to warm to room temperature and was stirred overnight. The solvent was removed and the residue extracted with $CH_2Cl_2$. The $CH_2Cl_2$ extract was washed with 2N citric acid, $H_2O$, 1N $NaHCO_3$, $H_2O$, brine and dried ($Na_2SO_4$). The solvent was removed to give 0.53 g of solid. Trituration with ethyl acetate gave 0.278 g of white solid, mp 184–186° C.

EXAMPLE 53

Ethyl 4-[(4-methoxybenzenesulfonyl)pyridin-3-ylmethylamino]-1,3-dimethyl-1H-pyrazolo[3,4-b] pyridine-5-carboxylate To a solution of 1.39 g (5 mmol) of (4-methoxybenzenesulfonyl)(3-pyridinylmethyl) amine in 4 ml of anhydrous 1-methyl-2-pyrrolidinone was added 0.2 g (5 mmol) of sodium hydride (60% in oil) and the mixture stirred at room temperature until gas evolution ceased. To this mixture was added 1.15 g (4.54 mmol) of ethyl 4-chloro-1,3-dimethylpyrazolo[3,4-b]pyridine-5-carboxylate and 2 ml of anhydrous 1-methyl-2-pyrrolidinone. The mixture was stirred in a sealed tube under nitrogen in an oil bath at 90° C. for 3 days. The mixture was cooled, poured into water and extracted with ethyl acetate. The extract was washed with H$_2$O, brine and dried (Na$_2$SO$_4$). The solution was filtered through a thin pad of hydrous magnesuim silicate and the filter pad washed with ethyl acetate. The filtrate was concentrated to dryness under vacuum to give 1.3 g of solid. Chromatography on silica gel with ethyl acetate as solvent gave 0.35 g of product as a solid, mp 152–154° C.

EXAMPLE 54

4-[(4-Methoxybenzenesulfonyl)pyridin-3-ylmethylamino]-1,3-dimethyl-1H-pyrazolo[3,4-b]pyridine-5-carboxylic Acid A mixture of 1.34 g (2.7 mmol) of ethyl 4-[(4-methoxybenzenesulfonyl)pyridin-3-ylmethylamino]-1,3-dimethyl-1H-pyrazolo[3,4-b]pyridin-5-carboxylate, 2.97 ml of 1N potassium hydroxide in 7.8 ml of ethanol and 4.83 ml of water was refluxed for 20 hr. Another 0.54 ml of 1N potassium hydroxide was added and the mixture refluxed 4 hrs. The solvent was removed under vacuum and toluene added and removed under vacuum. The residue was dissolved in water (20ml) and extracted with ethyl acetate. The aqueous layer was acidified with 2 N citric acid and the precipitated solid filtered off and washed with water. The solid was dried under vacuum to give 0.98 g of solid, mp 256–258° C.

EXAMPLE 55

4-[(4-Methoxybenzenesulfonyl)pyridin-3-ylmethylamino]-1,3-dimethyl-1H-pyrazolo[3,4-b]pyridine-5-carboxylic Acid, Potassium Salt A mixture of 0.34 g (0.68 mmol) of ethyl 4-[(4-methoxybenzenesulfonyl) pyridin-3-ylmethylamino]-1,3-dimethyl-1H-pyrazolo[3,4-b]pyridine-5-carboxylate and 0.748 ml of 1 N potassium hydroxide in 4 ml of ethanol-water (1:1) was refluxed for 24 hr. The solvent was removed under vacuum and to the residue was added toluene. The solvent was removed under vacuum to remove the water and the residue triturated with ethyl acetate to give the product as a solid, mp 160–167° C.

EXAMPLE 60

4-[(4-Methoxybenzenesulfonyl)pyridin-3-ylmethylamino]-1,3-dimethyl-1H-pyrazolo[3,4-b]pyridine-5-carboxylic Acid, Hydroxyamide A 1.5 g (2.459 mmol) sample of 4-[(4-methoxybenzenesulfonyl)pyridin-3-ylmethylamino]-1,3-dimethyl-1H-pyrazolo[3,4-b]pyridine-5-carboxylic acid was dissolved in 2.70 ml of 1N KOH. The water was removed by repeated additions and removal of toluene under vacuum to give 1.34 g of solid (potassium salt of the acid). A solution of 2.65 ml (5.3 mmol) of oxalyl chloride was cooled in an ice bath and 0.389 ml of N,N-dimethylformamide added dropwise. After 5 min. the 1.34 g of the previously prepared potassium salt was added and the mixture stirred for 10 min. in an ice bath and then allowed to warm to room temperature (mixture A). A mixture of 0.737 g (10.6 mmol) of hydroxylamine hydrochloride and 2.21 ml (15.9 mmol) of triethyamine in 9.39 ml of tetrahydrofuran and 2.45 ml of water was chilled in an ice bath (mixture B). The mixture A was chilled in an ice bath and added to the chilled and stirred mixture B. The mixture of A and B was stirred at 0° C. for 10 min and allowed to warm to room temperature and stir overnight. The solvent was removed under vacuum and the residue diluted with H$_2$O, acidified with 2 N citric acid and extracted with two 30-ml portions of CH$_2$Cl$_2$. The aqueous layer was neutrallized with solid NaHCO$_3$ to bring the pH to 7. The solid which precipitated was filtered and washed with H$_2$O to give 0.610 g of product as a solid, mp. 202–204° C. The CH$_2$Cl$_2$ extract was extracted with 2 N citric acid and the aqueous layer neutrallized with solid NaHCO$_3$. The precipitated solid was filtered off and washed with water to give 0.226 g of product, mp 196–198° C. (mass spectrum (ES) 483.5 (M+l).

EXAMPLE 61

4-[(4-Methoxybenzenesulfonyl)pyridin-3-ylmethylamino]-1,3-dimethyl-1H-pyrazolo[3,4-b]pyridine-5-carboxylic acid, Hydroxyamide Hydrochloride To a solution of 0.610 g (1.265 mmol) of 4-[(4-methoxybenenzenesulfonyl)pyridin-3-ylmethylamino]-1,3-dimethyl-5-carboxylic acid, hydroxyamide in 40 ml of CH$_2$Cl$_2$-methanol (1:1) cooled to 10° C. was added dropwise 1.51 ml of 1M hydrogen chloride in diethyl ether. The mixture was stirred at 10° C. for 10 min. and allowed to warm to room temperature for 1 hr. The solvent was removed under vacuum and toluene (2 ml) added twice and removed under vacuum after each addition. The residual solid was dried under vacuum to give 0.641 g of product as a solid, m.p. 170°–174° C.

EXAMPLE 62

4-[Benzyl-(4-methoxybenzenesulfonyl)amino]-1-phenyl-1H-pyrazolo[3,4-b]pyridine-5-carboxylic Acid, Hydroxyamide Following the procedure of Example 49, the product of Example 47 is reacted with benzyl-(4-methoxybenzenesulfonyl)amine and sodium hydride to provide ethyl 4-[benzyl-(4-methoxybenzenesulfonyl)amino]-1-phenyl-1H-pyrazolo[3,4-b]pyridine-5-carboxylate. m.p. 124°–126° C.

Following the procedure of Example 50, the above ester is hydrolyzed to provide 4-[benzyl-(4-methoxybenzenesulfonyl)amino]-1-phenyl-1H-pyrazolo[3,4-b]pyridine-5-carboxylic acid. m.p. 108–1 10° C.

Following the procedure of Example 52, the carboxylic acid is converted into the corresponding hydroxamic acid, 4-[benzyl-(4-methoxybenzenesulfonyl)amino]-1-phenyl-1H-pyrazolo[3,4-b]pyridine-5-carboxylic acid, hydroxyamide. m.p. 152°–154° C.

EXAMPLE 63

4-[(4-Methoxybenzenesulfonyl)pyridin-3-ylmethylamino]-1-phenyl-1H-pyrazolo[3,4-b]pyridine-5-carboxylic Acid, Hydroxyamide Following the procedure of Example 53, the product of Example 47 is reacted with (4-methoxybenzenesulfonyl) (3-pyridinylmethyl) amine and sodium hydride to provide ethyl 4-[(4-methoxybenzenesulfonyl)pyridin-3-ylmethylamino]-1-phenyl-1H-pyrazolo[3,4-b]pyridine-5-carboxylate. m.p. 89°–91° C.

Following the procedure of Example 54, the above ester is hydrolyzed to provide 4-[(4-methoxybenzenesulfonyl)pyridin-3-ylmethylamino]-1-phenyl-1H-pyrazolo[3,4b]pyridine-5-carboxylic acid. m.p. 136°–138° C.

Following the procedure of Example 60, the carboxylic acid is converted into the corresponding hydroxamic acid, 4-[(4-methoxybenzenesulfonyl)pyridin-3-ylmethylamino]-1-phenyl-1H-pyrazolo[3,4-b]pyridine-5-carboxylic acid, hydroxyamide. m.p. 114° C.(dec).

EXAMPLE 64

4-[(4-Methoxybenzenesulfonyl)pyridin-3-ylmethylamino]-1-phenyl-1H-pyrazolo[3,4-b]pyridine-5-carboxylic Acid, Hydroxyamide, Hydrochloride Following the procedure of Example 61, the product of Example 63 is converted into the corresponding hydrochloride salt. m.p. 161° C.(dec).

EXAMPLE 65

Ethyl 4-chloro-1-phenyl-3-methyl-1H-pyrazolo[3,4-b]pyridine-5-carboxylate

Following the procedure of Example 45, starting with 1-phenyl-3-methyl-5-aminopyrazole, diethyl{[(1-phenyl-3-methyl-5-pyrazolyl)amino]methylene}malonate is obtained. m.p. 70°–72° C.

Following the procedure of Example 46, the methylene malonate is converted into ethyl 4-hydroxy-1-phenyl-3-methyl-1H-pyrazolo[3,4-b]pyridine-5-carboxylate. m.p. 132°–134° C.

Following the procedure of Example 47, the hydroxy-ester is converted into the chloro-ester, ethyl-4-chloro-1-phenyl-3-methyl-1H-pyrazolo[3,4-b]pyridine-5-carboxylate. m.p. 108°–110° C.

EXAMPLE 66

4-[Benzyl-(4-methoxybenzenesulfonyl)amino]-1-phenyl-3-methyl-1H-pyrazolo[3,4b]pyridine-5-carboxylic Acid, Hydroxyamide Following the procedure of Example 49, the product of Example 65 is reacted with benzyl-(4-methoxybenzenesulfonyl)amine and sodium hydride to provide ethyl 4-[benzyl-(4-methoxybenzenesulfonyl)amino]-1-phenyl-3-methyl-1H-pyrazolo[3,4-b]pyridine-5-carboxylate. m.p. 164°–166° C.

Following the procedure of Example 50, the above ester is hydrolyzed to provide 4-[benzyl-(4-methoxybenzenesulfonyl)amino]-1-phenyl-3-methyl-1H-pyrazolo[3,4-b]pyridine-5-carboxylic acid. m.p. 246°–248° C.

Following the procedure of Example 52, the carboxylic acid is converted into the corresponding hydroxamic acid, 4-[benzyl-(4-methoxybenzenesulfonyl)amino]-1-phenyl-3-methyl-1H-pyrazolo[3,4-b]pyridine-5-carboxylic acid, hydroxyamide. m.p. 207°–210° C.

EXAMPLE 67

4-[(4-Methoxybenzenesulfonyl)pyridin-3-ylmethylamino]-1phenyl-3-methyl-1H-pyrazolo[3,4-b]pyridine-5-carboxylic Acid, Hydroxyamide Following the procedure of Example 53, the product of Example 65 is reacted with (4-methoxybenzenesulfonyl)(3-pyridinylmethyl) amine and sodium hydride to provide ethyl-4-[(4-methoxybenzenesulfonyl)pyridin-3-ylmethylamino]-1-phenyl-3-methyl-1H-pyrazolo[3,4-b]pyridine-5-carboxylate. m.p. 148°–150° C.

Following the procedure of Example 54, the above ester is hydrolyzed to provide 4-[(4-methoxybenzenesulfonyl)pyridin-3-ylmethylamino]-1-phenyl-3-methyl-1H-pyrazolo[3,4-b]pyridine-5-carboxylic acid. m.p. 235°–236° C.

Following the procedure of Example 60, the carboxylic acid is converted into the corresponding hydroxamic acid, 4-[(4-methoxybenzenesulfonyl)pyridin-3-ylmethylamino]-1-phenyl-3-methyl-1H-pyrazolo[3,4-b]pyridine-5-carboxylic acid, hydroxyamide. m.p. 192°–194° C.

EXAMPLE 68

4-[(4-Methoxybenzenesulfonyl)pyridin-3-ylmethylamino]-1phenyl-3-methyl-1H-pyrazolo[3,4-b]pyridine-5-carboxylic acid, hydroxyamide, hydrochloride Following the procedure of Example 61, the product of Example 67 is converted into the corresponding hydrochloride salt. m.p. 225°–226° C.

EXAMPLE 69

4-[(4-Methoxybenzenesulfonyl)pyridin-2-ylmethyl amino]-1,3-dimethyl-1H-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 70

4-[(4-Methoxybenzenesulfonyl)pyridin-4-ylmethylamino]-1,3-dimethyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 71

4-[(4-Methoxybenzenesulfonyl)pyridin-3-ylmethylamino]-1-isopropyl-1H-pyrazolo[3,4-b]pyridin-5-carboxylic acid, hydroxyamide.

Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 72

4-[(4-Methoxybenzenesulfonyl)pyridin-3-ylmethylamino]-1-benzyl-1H-pyrazolo[3,4-b]pyridin-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 73

4-[(4-Methoxybenzenesulfonyl)amino]-1-benzyl-3-methyl-1H-pyrazolo[3,4-b]pyridine-5-carboxylic acid, hydroxyamide Following procedures described in Examples 45–68 for the preparation of the (substituted-4-amino)1,3-dimethyl- 1H-pyrazolo[3,4-b]pyridine-5-carboxylic acid, hydroxyamides, the title compound may be prepared.

EXAMPLE 74

4-[(4-Methoxybenzenesulfonyl)2-thienylmethylamino]-1,3-dimethyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 75

4-[(4-Methoxybenzenesulfonyl)-3-thienylmethylamino]-1,3-dimethyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 76

4-[(4-Methoxybenzenesulfonyl)pyridin-3-ylmethylamino]-1-(2,4-dimethoxyphenyl)-3-methyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 77

4-[(4-Methoxybenzenesulfonyl)pyridin-3-ylmethylamino]-1-(2-methoxyphenyl)-3-methyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 78

4-{Methyl-[4-(4-pyridinyloxy)benzenesulfonyl]amino}-1,3-dimethyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 79

4-{Methyl-[4-(phenoxybenzenesulfonyl)amino]-1,3-dimethyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 80

4-[Methyl-(4-methoxybenzenesulfonyl)amino]-1,3-dimethyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 81

4-[Methyl-(4-propyloxybenzenesulfonyl)amino]-1,3-dimethyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 82

4-[(4-Methoxybenzenesulfonyl)pyridin-3-ylmethylamino]-1-methyl-3-phenyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 83

4-[(4-Methoxybenzenesulfonyl)pyridin-3-ylmethylamino]-1-ethyl-3-phenyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 84

4-[(4-Methoxybenzenesulfonyl)pyridin-3-ylmethylamino]-1-tert-butyl-3-methyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 85

4-[(4-Methoxybenzenesulfonyl)pyridin-3-ylmethylamino]-1-methyl-3-tert-butyl-1H-pyrazolo[3,4-b]pyridine-5-carboxylic acid, hydroxyamide Following procedures described in Examples 45–68 for the preparation of the (substituted-4-amino)1,3-dimethyl-1H-pyrazolo[3,4-b]pyridine-5-carboxylic acid, hydroxyamides, the title compound may be prepared.

EXAMPLE 86

4-[(4-Methoxybenzenesulfonyl)pyridin-3-ylmethylamino]-3-methylisothiazolo[5,4-b]pyridine-5-carboxylic Acid, Hydroxyamide To a stirred mixture of 0.366 g (8.4 mmol) of sodium hydride (60% in oil) in 10 ml of dry 1-methyl-2-pyrrolidinone was added (portionwise) 2.34 g (8.4 mmol) of methyl (4-methoxybenzenesulfonyl)pyridin-3-ylmethyl-amine. The mixture was stirred at room temperature until gas evolution ceased and 1.80 g of (7.0 mmol) of ethyl 4-chloro-3-methylisothiazolo[5,4-b]pyridine-5-carboxylate added. The mixture was heated at 80–90° C. for 44 hours, the solvent removed under vacuum and the residue diluted with water. The mixture was extracted with ethyl acetate and the extract washed with 2N citric acid, $H_2O$, 1 N $NaHCO_3$, brine and dried ($Na_2SO_4$). The solution was filtered through a thin pad of hydrous magnesium silicate and the pad washed with ethyl acetate. The filtrate was concentrated to dryness to give 2.39 g of ethyl 4-[(4-methoxybenzenesulfonyl)-pyridin-3-ylmethylamino]-3-methylisothiazolo[5,4-b]pyridine-5-carboxylate as a yellow solid, m.p. 142–144° C.

Anal. for $C_{23}H_{22}N_4O_5S_2$ Calc: C, 55.4; H, 4.5; N,11.2. Found: C, 55.5; H, 4.3; N,11.1.

Following the procedure of Example 54, a 2.25 g sample of the above ester was hydrolysed with KOH to give 0.46 g of 4-[(4-methoxybenzenesulfonyl)pyridin-3-ylmethylamino]-3-methylisothiazolo[5,4-b]pyridine-5-carboxylic acid as a white solid, m.p. 234–236° C.

Anal. for $C_{21}H_{18}N_4O_5S_2$ Calc: C, 53.6; H,3.9; N,11.9. Found: C, 53.5; H,3.8; N,1.8.

Following the procedure of Example 60, 2.0 g of the preceding compound as the potassium salt was converted to the title compound to give 0.39 g of off-white solid, m.p. 145–149° C. The hydrochloride salt was prepared from 0.27 g of the hydroxyamide according to the procedure of Example 61 to give 0.26 g of yellow solid, m.p. 224° C. dec.

Anal. for $C_{21}H_{19}N_5O_5S_2 \cdot HCl$ Calc: C, 48.3; H,3.9; N,13.4. Found: C, 48.0; H,3.8; N,13.2.

EXAMPLE 87

4-[(4-Methoxybenzenesulfonyl)pyridin-3-ylmethylamino]-3-methylisoxazolo[5,4-b]pyridine-5-carboxylic Acid, Hydroxyamide Following the procedure of Example 86, 1.7 g (7 mmol) of ethyl 4-chloro-3-methylisoxazolo[5,4-b]pyridine-5-carboxylate was reacted with 2.92 g (0.0105 mmol) of (4-methoxybenzenesulfonyl)pyridin-3-ylmethyl-amine to give 1.01 g of ethyl 4-[(4-methoxy-benzenesulfonyl)pyridin-3-yl-methylamino]-3-methylisoxazolo[5,4-b]pyridine-5-carboxylate as a white solid, m.p. 128–130° C.

Anal. for $C_{23}H_{22}N_4O_6S$: Calc: C, 57.3; H,4.6; N,11.6. Found: C, 57.3; H,4.7; N,11.5.

A mixture of 1.01 g (2.1 mmol) of the preceding compound in 10 ml of tetrahydrofuran and 2.93 ml of 1 N NaOH was stirred at room temperature overnight and the solvent removed. The residue was diluted with $H_2O$ and acidified with 2N citric acid (pH 4). The solid was filtered off and washed with $H_2O$ to give 0.88 g of 4-[(4-methoxybenzenesulfonyl)pyridin-3-ylmethylamino]-3-methylisoxazolo[5,4-b]pyridine-5-carboxylic acid as a white solid, m.p. 244–246° C.

Anal. for $C_{21}H_{18}N_4O_6S$: Calc: C, 55.5; H,4.0; N,12.3. Found: C, 55.2; H,4.0; N,12.2.

Following the procedure of Example 60, a 0.86 g (1.89 mmol) sample of the preceding compound was converted to the title compound to give 0.42 g of off-white solid, m.p. 150° C. dec.

Anal. for $C_{21}H_{19}N_5O_6S$: Calc: C, 53.7; H,4.1; N,14.9 Found: C, 53.4; H,4.5; N,14.4

The hydrochloride salt was prepared according to the procedure of Example 61 from 0.25 g of the title compound to give a solid which on trituration with ethyl acetate gave 0.27 g of off-white solid, m.p. 212–215° C.

Anal. for $C_{21}H_{19}N_5O_6S \cdot HCl$: Calc: C, 49.8; H,4.0; N,13.8 Found: C, 49.4; H,4.1; N,14.0

EXAMPLE 88

7-[(4-Methoxybenzenesulfonyl)pyridin-3-ylmethylamino]-2-methylpyrazolo[1,5-a]pyrimidine-6-carboxylic Acid, Hydroxyamide Following the procedure of Example 86, 1.8 (7.5 mmol) of ethyl 7-chloro-2-methyl pyrazolo[1,5-a]pyrimidine-6-carboxylate was reacted with 2.92 g (10.5 mmol) of (4-methoxybenzenesulfonyl)pyridin-3-ylmethyl-amine to give 1.64 g of ethyl 7-[(4-methoxybenzenesulfonyl)pyridin-3-ylmethylamino]-2-methylpyrazolo[1,5-a]pyrimidine-6-carboxylic acid as a yellow solid, m.p. 108–110° C.

Anal. for $C_{23}H_{23}N_5O_5S$ Calc: C, 57.4; H,4.8; N,14.5 Found: C, 54.5; H,4.7; N,14.4

A mixture of 1.54 g (3.20 mmol) of the preceding compound, tetrahydrofuran (15 ml) and 4.15 ml of 1 N NaOH was stirred at room temperature overnight and the solvent removed under vacuum. The residue was diluted with $H_2O$ and extracted with diethyl ether and ethyl acetate. The aqueous layer was acidified with 2 N citric acid (pH 5) and the solid filtered off and washed with $H_2O$. The solid was dried at 76° C. in a vacuum oven to give 1.03 g of 7-[(4-methoxybenzenesulfonyl)pyridin-3-ylmethylamino]-2-methylpyrazolo[1,5-a]pyrimidine-6-carboxylic acid as an off-white solid, m.p. 249–251° C.

Anal. for $C_{21}H_{19}N_5O_5S$ Calc: C, 55.6; H,4.2; N,15.4 Found: C, 55.2; H,4.2; N,15.6

A mixture of 1.0 g (2.2 mmol) of the preceding compound, 3 ml of $CH_3OH \cdot H_2O$ (2:1) and 2.43 ml of 1 N KOH was stirred 0.5 hours and the solvent removed under vacuum. Toluene (10 ml) was added three times and the solvent removed after each addition. The residue was dried in a vacuum oven and following the procedure of Example 60 the potassium salt was converted to the title compound to obtain 0.29 g of yellow solid, m.p. 185° C. dec.

Anal. for $C_{21}H_{20}N_6O_5S$ Calc: C, 53.8; H,4.3; N,17.9 Found: C, 53.9; H,4.4; N,17.3

The hydrochloride salt was prepared according to the procedure of Example 61 from 0.18 g of the title compound to give 0.22 g of yellow solid, m.p. 170° C. dec.

Anal. for $C_{21}H_{20}N_6O_5S \cdot HCl$ Calc: C, 50.0; H,4.2; N,16.6 Found: C, 48.7; H,4.4; N,16.1

EXAMPLE 89

4-{[4-(4-Chlorophenyloxy)benzenesulfonyl]methylamino}-1,3-dimethyl-1H-pyrazolo[3,4-b]pyridine-5-carboxylic Acid, Hydroxyamide To 20 ml of a 2 molar solution of methylamine in tetrahydrofuran chilled in an ice bath was added a solution of 5.16 g of 4-(4-chlorophenyloxy)benzene-sulfonyl chloride in 50 ml of tetrahydrofuran and 20 ml of $CH_2Cl_2$. The mixture was refluxed for 2 hours and the solvent removed under vacuum and the residue partitioned between $CH_2Cl_2 \cdot H_2O$ (1:1). The $CH_2Cl_2$ layer was separated and washed with 2 N citric acid, brine and dried ($Na_2SO_4$). The solution was filtered through a thin pad of hydrous magnesium silicate and the filter pad washed with $CH_2Cl_2$. The filtrate was concentrated to give 4.5 g of N-methyl-4-(4-chlorophenoxy)benzene-sulfonamide as a yellow solid, m.p. 80–83° C.

Following the procedure of Example 53, 1.79 g (6 mmol) of the preceding compound was reacted with 1.29 g (5 mmol) of ethyl 4-chloro-1,3-dimethyl pyrazolo[3,4-b]pyridine-5-carboxylate at 80–90° C. for 48 hours to give 3.12 g of solid. Chromatography on silica gel with hexane-diethyl ether (2:1) as eluent to give 1.92 g of ethyl 4-{[4-(4-chlorophenyloxy)benzenesulfonyl]methylamino}1,3-dimethyl-1H-pyrazolo[3,4-b]pyridine-5-carboxylate as an off-white solid, m.p. 52–55° C.

Anal. for $C_{24}H_{23}ClN_4O_5S$ Calc: C, 56.0; H,4.5; N,10.9 Found: C, 55.9; H,4.4; N,10.6

A mixture of 1.90 g (3.69 mmol) of the preceding ester and 4.05 ml (4.06 mmol) of 1 N KOH in 15 ml of tetrahydrofuran was stirred at room temperature for 2 days and then 0.75 ml of 1 N KOH was added and the mixture was refluxed overnight. The solvent was removed under vacuum and the toluene (25 ml) added to the residue and removed under vacuum. The residue was triturated with ethyl acetate and the solid filtered and dried under vacuum to give 1.6 g of 4-{[4-(4-chlorophenyloxy) benzenesulfonyl]methylamino}-1,3-dimethyl-1H-pyrazolo[3,4-b]pyridine-5-carboxylic acid, potassium salt. Following the procedure of Example 52, 1.60 g of the preceding potassium salt was converted to the title compound to obtain 1.82 g of solid. This solid was purified on thick layer silica gel plates with 4% $CH_3OH$ in ethyl acetate as solvent to give 0.59 g of light yellow solid, m.p. 120° C. dec.

Anal. for $C_{22}H_{20}ClN_5O_5S \cdot H_2O$ Calc: C, 51.7; H,4.3; N,13.7 Found: C, 51.2; H,4.0; N,13.6

EXAMPLE 90

4-{[4-(4-Chlorophenyloxy)benzenesulfonyl]methylamino}-3-methylisothiazolo[5,4-b]pyridine-5-carboxylic Acid Hydroxyamide Following the procedure of Example 86, 1.17 g (38.5 mmol) of N-methyl-4-(4-chlorophenoxy)benzenesulfonamide was reacted with 0.916 g (3.57 mmol) of ethyl 4-chloro-3-methylisothiazolo[5,4-b]pyridine-5-carboxylate for 33 hours to give a solid which was triturated with ethyl acetate to give 0.99 g of ethyl 4-{[4-(4-chlorophenyloxy)benzenesulfonyl]methylamino}-3-methylisothiazolo[5,4-b]pyridine-5-carboxylate as a white solid, m.p. 117–120° C.

Anal. for $C_{23}H_{20}ClN_3O_5S_2$ Calc: C, 53.3; H,3.9; N,8.1 Found: C, 53.2; H,3.9; N,7.8

Following the procedure of Example 54, a mixture of 0.96 g (1.85 mmol) of the preceding compound and 2.40 ml of 1 N KOH in 15 ml of tetrahydrofuran-ethanol (2:1) was refluxed 16 hours and the solvent removed under vacuum. Toluene (25 ml) was added to the residue and the solvent removed. The residue was triturated with ethyl acetate to give a solid which was dried under vacuum to give 0.80 g of 4-{[4-(4-chlorophenyloxy)-benzenesulfonyl]methylamino}-3-methylisothiazolo[5,4-b]pyridine-5-carboxylic acid, potassium salt. Following the procedure of Example 52, 0.80 g (1.51 mmol) of the preceding compound was converted to the title compound to give 0.82 g of solid. This solid was chromatographed on thick layer silica gel plates with 4% $CH_3OH$ in ethyl acetate as solvent to give 0.19 g of solid which was triturated with hexane to give 0.12 g of 115° C. dec.

Anal. for $C_{21}H_{17}ClN_4O_5S_2 \cdot ¼$ hexane Calc: C, 51.3; H,3.9; N,10.6 Found: C, 51.9; H,4.2; N,10.4

EXAMPLE 91

4-{Methyl-[4-(4-pyridinyloxy)benzenesulfonyl]amino}-1,3-dimethyl-1H-pyrazolo[3,4-b]pyridine-5-carboxylic Acid, Hydroxyamide A suspension of 35 g of [4-(4-pyridinyloxy) benzenesulfonyl chloride hydrochloride in 800 ml of tetrahydrofuran was added slowly to 163 ml of 2 M methylamine in tetrahydrofuran. An additional 550 ml of tetrahydrofuran was added and the suspension refluxed for 3 hours. The solvent was removed under vacuum and the residue partitioned between $CH_2Cl_2$ and $H_2O$. The organic layer was separated, washed with saturated $NaHCO_3$, brine and dried ($Na_2SO_4$). The solvent was removed to give 13.11 g of N-methyl-4-(pyridin-4-yloxy)benzenesulfonamide, m.p. 125–127° C. The aqueous layer was neutralized with 1 N NaOH (solid precipitated) and extracted with $CH_2Cl_2$. The extract was washed with brine and dried ($Na_2SO_4$). The solvent was removed to give an additional 15.9 g of N-methyl-4-(pyridin-4-yloxy)benzenesulfonamide. A 2.80 g (10.6 mmol) portion of the preceding compound was added to a stirred suspension of 0.424 g (10.6 mmol) of sodium hydride (60% in oil) in 20 ml of dry 1-methylpyrrolidinone. The mixture was stirred until gas evolution ceased and 2.8 g (10.0 mmol) of ethyl 4-chloro-1,3-dimethyl-1H-pyrazolo[3,4-b]pyridine-5-carboxylate was added followed by the addition of 20 ml of dry 1-methylpyrrolidinone. The mixture was heated at 80–90° C. for 58 hours. The solvent was removed under vacuum and the residue extracted with ethyl acetate (100 ml) and the extract washed with 100 ml of $H_2O$. The extract was stirred with 40 ml of 1 N HCl for 1 hour and the aqueous layer separated and neutralized (pH 6–7) with 1 N $NaHCO_3$. The mixture was extracted with ethyl acetate and the extract washed with $H_2O$, brine and dried ($Na_2SO_4$). The solution was filtered through a thin pad of hydrous magnesium silicate and the filter pad washed with ethyl acetate. The filtrate was concentrated to dryness and the residue crystallized with ethyl acetate-hexane to give 3.43 g of ethyl 4-{methyl-[4-(4-pyridinyloxy)benzenesulfonyl]amino}-1,3-dimethyl-1H-pyrazolo[3,4-b]pyridine-5-carboxylate as pale yellow crystals, m.p. 117–119° C.

Anal. for $C_{23}H_{23}N_5O_5S$ Calc: C, 57.4; H,4.8; N,14.5. Found: C, 57.3; H,4.7; N,14.5.

A mixture of 7.44 g (15.5 mmol) of the preceding compound and 18.54 ml of 1 N KOH in 100 ml tetrahydrofuran-ethanol (6:4) was refluxed overnight under nitrogen. The solvent was removed and toluene and ethanol added and the solvent removed under vacuum. The residue was triturated with diethyl ether, filtered and the solid dried under vacuum to give 7.57 g of the potassium salt of 4-{methyl-[4-(4-pyridinyloxy)benzene-sulfonyl]amino}-1,3-dimethyl-1H-pyrazolo[3,4-b]pyridine-5-carboxylic acid. A 0.18 g sample of the preceding compound was dissolved in $H_2O$ and the solution brought to pH 6 with 2 N citric acid. The precipitated solid was filtered, washed with $H_2O$ and dried under vacuum to give 0.045 g of 4-{methyl-[4-(4-pyridinyloxy)benzene-sulfonyl]amino}-1,3-dimethyl-1H-pyrazolo[3,4-b]pyridine-5-carboxylic acid as a white solid, m.p. 171–185° C.

Anal. for $C_{21}H_{19}N_5O_5S \cdot 2 \ H_2O$ Calc: C, 51.5; H,4.7; N,14.3 Found: C, 51.8; H,4.1; N,14.2

To a chilled (0° C.) mixture of 2.2 ml (4.4 mmol) of oxalyl chloride in $CH_2Cl_2$ (2 M) was added dropwise 0.308 ml (4.0 mmol) of N,N-dimethylformamide followed by the addition of 0.982 g (2 mmol) of the preceding potassium salt and 10 ml of $CH_2Cl_2$ (Mixture A). A mixture of 0.444 ml (8 mmol) of hydroxylamine in $H_2O$ (50% w), 0.634 ml of triethylamine and 3.50 ml of tetrahydrofuran was chilled and added to the chilled Mixture A. After stirring at 0° C. for 15 min., the mixture was stirred at room temperature overnight. The solvent was removed and the residue partitioned between 10 ml of $CH_2Cl_2$ and 30 ml of $H_2O$. The solid was filtered off and suspended in $H_2O$. The pH of the mixture was adjusted to pH 6–7 with 2 N citric acid, stirred, filtered and the solid washed with $H_2O$ and $CH_2Cl_2$ to give 0.47 g of 4-{methyl-[4-(4-pyridinyloxy)benzenesulfonyl]amino}-1,3-dimethyl-1H-pyrazolo[3,4-b]pyridine-5-carboxylic acid, hydroxyamide as a white solid, m.p. 147° dec.

Anal. for $C_{21}H_{20}N_6O_5S \cdot H_2O$ Calc: C, 51.8; H,4.6; N,17.3 Found: C, 51.3; H,4.8; N,17.4

To a cooled 2.2 g (4.7 mmol) sample of the preceding compound in 40 ml of $CH_2Cl_2$—$CH_3OH$ (1:1) was added 5.64 ml of 1 M HCl in diethyl ether. The mixture was stirred in an ice bath for 10 min. and then at room temperature for 1 hour. The solvent was removed under vacuum and 25 ml of toluene added (two times) and removed under vacuum. The solid was triturated with 20 ml of methanol to give 1.60 g of the product of the Example as a white solid, m.p. 197–200° C.

Anal. for $C_{21}H_{20}N_6O_5S \cdot HCl \cdot H_2O$ Calc: C, 48.2; H,4.4; N,16.1 Found: C, 47.7; H,4.7; N,15.9

EXAMPLE 92

4-{Methyl-[4-(4-pyridinyloxy)benzenesulfonyl]amino}-3-methylisothiazolo[5,4-b]pyridine-5-carboxylic Acid, Hydroxyamide Following the procedure of Example 86, 1.28 g (5mmol) of ethyl 4-chloro-3-methylisothiazolo[5,4-b]pyridine-5-carboxylate was reacted with 1.4 g (5.3 mmol) of N-methyl-4-(pyridin-4-yloxy)benzenesulfonamide to give 2.78 g of an oil. This oil was dissolved in 10 ml of ethyl acetate and 13 ml of 1 N HCl added. The organic layer was separated. The aqueous layer was brought to pH 6 with 1 N NaOH and extracted with 40 ml of $CH_2Cl_2$. The $CH_2Cl_2$ extract was washed with brine and dried ($Na_2SO_4$). The solvent was removed to give 1.69 g of solid which was chromatographed on silica gel with ethyl acetate as solvent to give 0.95 g of ethyl 4-{methyl-[4-(4-pyridinyloxy)benzene-sulfonyl]amino}-3-methylisothiazolo[5,4-b]pyridine-5-carboxylate as a yellow solid, m.p. 57–60° C.

Anal. for $C_{22}H_{20}N_4O_5S_2$ Calc: C, 54.5; H,4.2; N,11.6 Found: C, 54.4; H,4.1; N,11.2

Following the procedure of Example 50, a mixture of 0.95 g of the preceding ester and 2.8 ml of 1 N KOH in 2.5 ml of tetrahydrofuran and 25 ml of ethanol was refluxed 24 hours and the solvent removed under vacuum to give 1.0 g of solid. Following the procedure of Example 91, a 0.82 g sample of the resulting potassium salt was reacted with hydroxylamine to give 0.78 g of solid. Chromatography on thick layer silica gel plates with ethyl acetate-$CH_3OH$ (85:15) as solvent gave 0.22 g of 4-{methyl-[4-(4-pyridinyloxy)benzenesulfonyl]amino}-3-methylisothiazolo[5,4-b]pyridine-5-carboxylic acid, hydroxyamide as an off-white solid, m.p. 146° C. dec.

Anal. for $C_{20}H_{17}N_5O_5S_2 \cdot \frac{1}{2} H_2O$ Calc: C, 50.0; H,3.8; N,14.6 Found: C, 49.7; H,4.0; N,13.8

To a solution of 0.20 g of the preceding compound in 3.4 ml of $CH_2Cl_2$—$CH_3OH$ (1:1) was added 0.508 ml of 1 N HCl in diethyl ether. The solvent was removed under vacuum and the solid dried 20 hours under vacuum to give the hydrochloride salt of the title compound as an off-white solid, m.p. 186° C. dec.

Anal. for $C_{20}H_{17}N_5O_5S_2 \cdot HCl \cdot H_2O$ Calc: C, 45.6; H,3.8; N,13.3. Found: C, 45.6; H,4.1; N,12.7.

EXAMPLE 93

4-{Methyl-[4-(4-pyridinyloxy)benzenesulfonyl]amino}-1-methyl-3-phenyl-1H-pyrazolo[3,4-b]pyridine-5-carboxylic acid, Hydroxyamide Following the procedure described in Example 91, 1.45 g (5.5 mmol) of N-methyl-4-(pyridinyl-4-oxy)benzenesulfonamide was reacted with 1.58 g (5 mmol) of ethyl 4-chloro-1-methyl-3-phenyl-1H-pyrazolo[3,4-b]pyridine-5-carboxylate in 20 ml of 1-methyl-pyrrolidinone to give 1.62 g of ethyl 4-{methyl-[4-(4-pyridinyloxy)benzenesulfonyl]-amino}-1-methyl-3-phenyl-1H-pyrazolo[3,4-b]pyridine-5-carboxylate as an off-white solid, m.p. 128–131° C.

Anal. for $C_{28}H_{25}N_5O_5S$ Calc: C, 61.9; H,4.6; N,12.9 Found: C, 61.7; H,4.7; N,12.8

A mixture of 1.60 g (2.94 mmol) of the preceding compound and 3.53 ml of 1 N KOH in 8 ml of tetrahydrofuran-ethanol (1:1) was refluxed overnight and the solvent removed. The residue was triturated with diethyl ether to give 1.62 g of potassium 4-{methyl-[4-(4-pyridinyloxy)benzenesulfonyl]amino}-1-methyl-3-phenyl-1H-pyrazolo[3,4-b]pyridine-5-carboxylate as solid.

Following the procedure of Example 91, a 1.47 g (2.66 mmol) sample of the preceding compound was reacted with hydroxylamine to give 0.49 g of solid. This solid (0.45 g) was dissolved in 15 ml of $CH_2Cl_2$—$CH_3OH$ (1:1) and to the chilled solution was added 2.26 ml of 1 N HCl in diethyl ether. The mixture was stirred at room temperature for 1 hour and the solvent removed to give the hydrochloride salt of the title compound as an off-white solid, m.p. 195° C. dec.

Anal. for $C_{26}H_{22}N_6O_5S \cdot HCl \cdot H_2O$ Calc: C, 53.4; H,5.0; N,14.4 Found: C, 53.2; H,4.3; N,14.3

EXAMPLE 94

4-{Methyl-[4-(4-pyridinyloxy)benzenesulfonyl]amino}-3-methylisoxazolo[5,4-b]pyridine-5-carboxylic acid, Hydroxyamide, Following the procedure of Example 91, 1.45 g (5.5 mmol) of N-methyl-4-(pyridinyl-4-oxy)benzenesulfonamide was reacted with 1.20 g (5 mmol) of ethyl 4-chloro-3-methylisoxazolo[5,4-b]pyridine-5-carboxylate to give 1.29 g of ethyl 4-{methyl-[4-(4-pyridinyloxy)-benzenesulfonyl]amino}-3-methylisoxazolo[5,4-b]pyridine-5-carboxylate as an off-white solid, m.p. 155–157° C.

Anal. for $C_{22}H_{20}N_4O_6S \cdot \frac{1}{2} H_2O$ Calc: C, 55.3; H,4.4; N,11.7 Found: C, 55.2; H,4.3; N,11.6

A mixture of 1.84 g (3.92 mmol) of the preceding ester and 4.71 ml of 1 N KOH in 10 ml of tetrahydrofuran-ethanol (1:1) was refluxed overnight and the solvent removed under vacuum. The residue was triturated with diethyl ether and filtered to give 1.59 g of potassium 4-{methyl-[4-(4-pyridinyloxy)benzene-sulfonyl]amino}-3-methylisoxazolo[5,4-b]pyridine-5-carboxylate as a pale yellow solid. Following the procedure of Example 91, the preceding potassium salt (1.45 g) was reacted with hydroxylamine to give a solid. The solid was partitioned between 30 ml of $CH_2Cl_2$ and 30 ml of $H_2O$ and filtered. The $CH_2Cl_2$ layer was stirred with 2 N citric acid (aqueous phase-pH 6). The solid which precipitated was filtered off and suspended in $H_2O$. The aqueous suspension was adjusted to pH 7 with 1 N $NaHCO_3$ and filtered. The solid was again suspended in $H_2O$ and the pH of the aqueous suspension adjusted to pH 6 with 2 N citric acid. The mixture was stirred and filtered to give 0.66 g of 4-{methyl-[4-(4-pyridinyl-oxy)benzenesulfonyl]amino}-3-methylisoxazolo[5,4-b]pyridine-5-carboxylic acid, hydroxyamide, m.p. 141° C. dec.

Anal. for $C_{26}H_{22}N_6O_5S \cdot H_2O$ Calc: C, 58.9; H,4.4; N,15.3 Found: C, 56.3; H,4.3; N,15.2

To a chilled solution of 0.569 g (1.25 mmol) of the preceding hydroxyamide in 10 ml of $CH_2Cl_2$—$CH_3OH$ (1:1) was added 1.50 ml of 1 N HCl in diethyl ether. The mixture was stirred at room temperature for 1 hour and the solvent removed to give 0.582 g of the hydrochloride salt of the title compound as a light brown solid, m.p. 170° C. dec.

Anal. for $C_{20}H_{17}N_5O_6S \cdot HCl \cdot H_2O$ Calc: C, 47.1; H,4.0; N,13.7 Found: C, 47.2; H,4.5; N,13.2

EXAMPLE 95

7-{Methyl-[4-(4-pyridinyloxy)benzenesulfonyl]amino}-2-methylpyrazolo[1,5-a]pyrimidine-6-carboxylic acid, Hydroxyamide Following the procedure of Example 86, 1.19 g (5 mmol) of ethyl 7-chloro-2-methylpyrazolo[1,5-a]pyrimidine-6-carboxylate was reacted with 1.45 g (5.5 mmol) of N-methyl-4-(pyridinyl-4-oxy)benzenesulfonamide (as the sodium salt) in 20 ml of 1-methylpyrrolidinone at 80–90° C. for 66 hours. The solvent was removed and the residue partitioned between 30 ml of ethyl acetate and 30 ml of $H_2O$. The organic layer was separted and stirred with 30 ml of 1 N HCl for 1 hour and filtered. The aqueous layer was separated and the pH adjusted to pH 6 with saturated $NaHCO_3$ solution. The mixture was extracted with ethyl acetate and the extract washed with brine and dried ($Na_2SO_4$). The solution was filtered through a thin pad of hydrous magnesium silicate and the filter pad washed with ethyl acetate. The filtrate was concentrated to dryness and the solid suspended in 50 ml of $H_2O$ and the pH of the stirred suspension adjusted to pH 7 with 1 N $NaHCO_3$. The mixture was extracted with ethyl acetate and the extract washed with brine and dried ($Na_2SO_4$). The solution was filtered through a thin pad of hydrous magnesium silicate and the filtrate concentrated to dryness to give 1.35 g of ethyl 7-{methyl-[4-(4-pyridinyloxy)-benzenesulfonyl]amino}-2-methylpyrazolo[1,5-a]pyrimidine-6-carboxylate as a yellow solid, m.p. 139–144° C.

Anal. for $C_{22}H_{21}N_4O_5S$ Calc: C, 56.5; H,4.5; N,15.0 Found: C, 56.8; H,4.6; N,14.9

A mixture of 1.25 g (2.67 mmol) of the preceding ester and 3.21 ml of 1 N KOH in 15 ml of tetrahydrofuran was stirred at room temperature overnight. The mixture was filtered and the solid washed with diethyl ether and ethyl acetate to give 0.5 g of potassium 7-{methyl-[4-(4-pyridinyloxy)benzene-sulfonyl]amino}-2-methylpyrazolo[1,5-a]pyrimidine-6-carboxylate. A 0.15 g sample of the preceding compound was dissolved in water and the pH adjusted to pH 6 with 2 N citric acid. The mixture was filtered to give 0.12 g of 7-{methyl-[4-(4-pyridinyloxy)benzenesulfonyl]amino}-2-methylpyrazolo[1,5-a]pyrimidine-6-carboxylic acid as a white solid, m.p. 246–248° C.

Anal. for $C_{20}H_{17}N_5O_5S$ Calc: C, 54.7; H,3.9; N,15.9 Found: C, 54.2; H,4.1; N,16.4

Following the procedures of Example 91, the title compound is prepared from the carboxylic acid described above.

EXAMPLE 96

4-{Methyl-[4-(4-pyridinyloxy)benzenesulfonyl]amino}-7-methyl-1,8-naphthyridine-3-carboxylic Acid, Hydroxyamide A mixture of 10.8 g (0.1 M) of 2-amino-6-methylpyridine and 23.78 g (0.12 M) of diethyl ethoxymethylenemalonate was heated in an oil bath (preheated to 90° C.) for 1 hr. The mixture was cooled to room temperature and the solid was recrystallized from 100 ml of ethanol to give 26.38 g of 2-(2,2-dicarbethoxy-1-vinylamino)-6-methylpyridine, m.p. 102–104° C. Reported m.p. 107–108° C. (U.S. Pat. No. 4,166,817 issued Sep. 4, 1979). A solution of 20.79 g of the preceding compound in 40 ml of Dowtherm (heated to 80° C.) was dropped into 100 ml of Dowtherm which had been preheated to 258° C. The temperature of the mixture dropped to 200° C. and after the temperature returned to 250° C. (10 min), the mixture was heated at 250° C. for 30 min. The mixture was immediately cooled to room temperature and allowed to stand overnight. The mixture was filtered and the solid washed with hexane and $CH_2Cl_2$ to give 4.24 g of ethyl 4-hydroxy-7-methyl-1,8-naphthyridine-3-carboxylate as a brown solid.

A mixture of 4.2 g (0.018 M) of the preceding compound and 45 ml of $POCl_3$ (0.48 M) was heated at 70–80° C. for 4 hours. The solution was concentrated under vacuum and the residue poured onto crushed ice. The resulting mixture was neutralized with 5 N NaOH to pH 6 and extracted with diethyl ether (3×250 ml). The extract was washed with brine and dried over $Na_2SO_4$. The solvent was removed under vacuum to give 2.24 g of ethyl 4-chloro-7-methyl-1,8-naphthyridine-3-carboxylate as a yellow solid, m.p. 72–74° C.: reported m.p. 92–93° C. (dec) (U.S. Pat. No. 4,166,817).

To a mixture (under nitrogen) of 0.22 g (5.5 mmol) of NaH (60% in oil) in 20 ml of 1-methylpyrrolidinone was added 1.45 g (5.5 mmol) of N-methyl-4-(pyridin-4-yloxy)benzenesulfonamide. After gas evolution ceased, 1.25 g (5 mmol) of ethyl 4-chloro-7-methyl-1,8-naphthyridine-3-carboxylate was added. The mixture was heated at 80–90° C. for 60 hrs and the solvent removed under vacuum. The residue was partitioned between $H_2O$ and ethyl acetate and the mixture filtered through diatomaceous earth. The organic layer of the filtrate was separated and washed with $H_2O$ and dried ($Na_2SO_4$). The solution was filtered through a thin pad of hydrous magnesium silicate and the filtrate concentrated under vacuum to give 0.97 g of a brown solid (mass spectrum 265 (75%); 479 (25%). The product (mass spectrum (M+H) 479) is separated by chromatography on silica gel and following the procedure of Example 91 is converted to the title compound.

EXAMPLE 97

7-{Methyl-[4-(4-pyridinyloxy)benzenesulfonyl]amino}-2,3-dimethylimidazo[4,5-b]pyridine-6-carboxylic Acid, Hydroxyamide Following the general procedure described in J. Chem. Soc. Perkin Trans. 1, 2789 (1992) a mixture of 1,2-dimethyl-5-nitroimidazole (8.46 g; 0.06 M), diethyl ethoxymethylenemalonate (13.08 g; 0.06 M) and 2.11 g of 5% Pd on carbon in 135 ml of dioxane was reduced in a Parr Hydrogenator at 35 to 40 psi of hydrogen for 29 hours. The mixture was filtered through diatomaceous earth and the solvent removed to give a brown oil. This oil was dissolved in 100 ml of 2 N HCl and the pH adjusted to pH 5 with 10 N NaOH. The mixture was extracted twice with 100 ml of ethyl acetate (extract discarded). The pH was adjusted to pH 7 and extracted with 150 ml of ethyl acetate and then the pH was adjusted to pH 9 and again extracted twice with 150 ml of ethyl acetate. The pH 7 and pH 9 extracts were combined and washed with brine and dried over $Na_2SO_4$. The solution was filtered through a thin pad of hydrous magnesium silicate and the filtrate concentrated to dryness to give 7.61 g of 5-[2,2-bis(ethoxycarbonyl)-1-vinylamino]-1,2-dimethylimidazole (diethyl[(1,2-dimethylimidazol-5-yl)aminomethylene]malonate) as a brown oil.

A mixture of the preceding compound (7.9 g) and 35 ml of $POCl_3$ was refluxed for 7 hours under nitrogen and then concentrated under vacuum. The black residue was poured onto crushed ice (with stirring) and the mixture brought to pH 5 with 5 N NaOH. The mixture was extracted with 150 ml of ethyl acetate, 200 ml of diethyl ether and 200 ml of $CH_2Cl_2$. Each extract was washed with 1 N $NaHCO_3$, brine and dried ($Na_2SO_4$). The solutions were combined and filtered through a thin pad of hydrous magnesium silicate. The filtrate was concentrated to dryness under vacuum to give 4.1 g of ethyl 7-chloro-2,3-dimethylimidazo[4,5-b]pyridine-6-carboxylate as a tan solid, m.p. 85–90° C. A sample crystallized from diethyl ether gave crystals, m.p. 117–119° C., Anal. for $C_{11}H_{12}ClN_3O_2 \cdot \frac{1}{2} H_2O$ Calc. C, 48.8; H,4.6; N,15.9 Found C, 50.3; H,5.6; N,16.0

Following the procedure of Example 91, a 0.759 g (3 mmol) portion of the preceding ester was heated at 80–90° C. in 14 ml of 1-methylpyrrolidinone with the sodium salt of N-methyl-4-(pyridin-4-yloxy)benzenesulfonamide[from 0.871 g; 3.3 mmol of N-methyl-4-(pyridin-4-yloxy) benzenesulfonamide and 79.2 mg (3.3 mmol) of NaH (60% in oil)]. The mixture was heated for 2.5 days at 80–90° C. and 3 hrs at 100° C. and then the solvent was removed under vacuum. The residue was extracted with ethyl acetate and the extract washed with $H_2O$. The organic layer was stirred with 1 N HCl (30 ml) for 0.5 hour and the aqueous layer separated and brought to pH 6 with 5 N NaOH. The mixture was extracted with ethyl acetate and the extract dried over $Na_2SO_4$. The solvent was removed under vacuum to give 1.0 g of a brown oil which contained the product ethyl 7-{methyl-[4-(4-pyridinyloxy)benzenesulfonyl]amino}-2,3-dimethyl-imidazo[4,5-b]pyridine-6-carboxylate; mass spectrum (ES) 479.1 (M+H). Following the procedure of Example 91, the preceding compound is converted to the title compound.

EXAMPLE 98

2-Methyl-4-{methyl-[4-(4-pyridinyloxy) benzenesulfonyl]amino}thieno[3,4-b]pyridine-3-carboxylic Acid, Hydroxyamide A mixture of 10.0 g (63.6 mmol) of methyl 3-aminothiophene-4-carboxylate, 10.1 g (63.6 mmol) of ethyl (trans)-3-ethoxycrotonate and 40 mg of p-toluenesulfonic acid, monohydrate in 50 ml of p-xylenes was refluxed overnight and the solvent removed under vacuum. To the residue was added 20 ml of p-xylenes, and 23.7 ml of $NaOC_2H_5$ (21% by wt) (63.6 mmol) in ethanol and the mixture refluxed for 3 hrs. The solvent was removed, the residue diluted with $H_2O$ and the pH adjusted to pH 4 with 1 N HCl. The precipitate was filtered, washed with water and ethyl acetate to give 4.95 g of 4-hydroxy-2-methyl-thieno[3,4-b]pyridine-3-carboxylic acid as a brown solid.

The preceding compound (1.4 g) was dissolved in 10 ml of dry methanol and HCl gas bubbled into the solution for 10 min. The solution was stirred overnight at room temperature and the solvent removed under vacuum. The residue was dissolved in ethyl acetate and the solution washed with saturated $NaHCO_3$, brine and dried ($Na_2SO_4$). The solvent was removed to give a solid which was triturated with ethyl acetate. The mixture was cooled and filtered to give 0.765 g of methyl 4-chloro-2-methylthieno[3,4-b]pyridine-3-carboxylate as a yellow solid.

Following the procedure of Example 91, the preceding compound is converted to the title compound.

EXAMPLE 99

5-Methyl-7-{methyl-[4-(4-pyridinyloxy) benzenesulfonyl]amino}-thieno[3,2-b]pyridine-6-carboxylic Acid, Hydroxyamide Following the procedure described in J. Med. Chem. 33, 2640 (1990), a mixture of 10 g (63.6 mmol) of methyl 3-aminothiophene-2-carboxylate (10.1 g) (63.6 mmol) of ethyl (trans)-3-ethoxycrotonate and 40 mg of p-toluenesulfonic acid monohydrate in 80 ml of xylene was refluxed overnight. The solvent was removed under vacuum and the residue dissolved in ethyl acetate. The solution was washed with $H_2O$, 2 N citric acid, 1 N $NaHCO_3$, brine and dried ($Na_2SO_4$). The solid 16 g was chromatographed on silica gel with hexane-ethyl acetate (5:1) to give 6.65 g of ethyl 3-[(2-methyoxycarbonyl-3-thienyl)amino]crotonate as a yellow oil. To a sample of 0.269 g (1 mmol) of the preceding compound in 3.5 ml of xylenes (chilled in an ice bath) was added 44 mg (1.1 mmol) of NaH (60% in oil). The mixture was refluxed for 3 hours and the solvent removed. The residue diluted with water and extracted with ethyl acetate. The aqueous layer was acidified (1 N HCl) to pH 4 and the mixture extracted with ethyl acetate. The extract was washed with brine, dried over $Na_2SO_4$ and the solvent removed to give 190 mg of a mixture (1:1) of methyl 7-hydroxy-5-methylthieno[3,2-b]pyridine-6-carboxylate and ethyl 7-hydroxy-5-methylthieno[3,2-b]pyridine-6-carboxylate as a solid. The preceding ethyl ester was prepared in the following manner.

A mixture of 5.0 g (31.8 mmol) of methyl 3-aminothiophene-2-carboxylate, 5.03 g (31.8 mmol) of ethyl (trans)-3-ethoxycrotonate and 20 mg of p-toluenesulfonic acid monohydrate in 50 ml of p-xylenes was refluxed 1 hour and allowed to stand 2 days at room temperature. The mixture was concentrated under vacuum and then cooled (ice bath). To the solution was added 12.4 ml of a solution of sodium ethoxide (21% by wt) in ethanol. The mixture was refluxed for 2 hours and the solvent removed. The residue was partitioned between $H_2O$ and diethyl ether and the $H_2O$ layer separated and acidified to pH 4 with 1 N HCl. The mixture was extracted with ethyl acetate and the extract washed with brine and dried ($Na_2SO_4$). The solvent was removed to give 2.2 g of brown solid. The solid was triturated with ethyl acetate, chilled and filtered to give 1.0 g of ethyl 7-hydroxy-5-methylthieno[3,2-b]pyridine-6-carboxylate as a light tan solid (mass spectrum (ES) 238 (M+H).

A mixture of the preceding compound (0.985 g) and 4 ml of $POCl_3$ was refluxed 2 hours and the mixture poured onto crushed ice. The mixture was extracted with ethyl acetate and the extract concentrated to dryness. The residue was dissolved in $CH_2Cl_2$ and the solution washed with $H_2O$ and dried over $Na_2SO_4$. The solution was filtered through a thin pad of hydrous magnesium silicate and the filtrate concentrated to dryness to give 0.62 g of ethyl 7-chloro-5-methylthieno[3,2-b]pyridine-6-carboxylate as a yellow oil; thin layer chromatography on silica gel; Rf=0.9; ethyl acetate-hexane (1:1).

Following the procedure of Example 86, the preceding compound is reacted with N-methyl-4-(pyridin-4-yloxy) benzenesulfonamide to give ethyl 5-methyl-7-{methyl-[4-(4-pyridinyloxy) benzenesulfonyl]amino}thieno[3,2-b] pyridine-6-carboxylate. As described for Example 91, the preceding compound is converted to the title compound.

Representative compounds of this invention were evaluated as inhibitors of the enzymes MMP-1, MMP-9, MMP-13 and TNF-(α converting enzyme (TACE). The standard pharmacological test procedures used, and results obtained which establish this biological profile are shown below.

Test Procedures for Measuring MMP-1, MMP-9, and MMP-13 Inhibition

These standard pharmacological test procedures are based on the cleavage of a thiopeptide substrates such as Ac-Pro- Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with buffer (50 mM HEPES, pH 7.5, 5 mM $CaCl_2$, 0.02% Brij) to the desired final concentration. The buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 nm HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generated using multiple doses of drug and $IC_{50}$ values with 95% CI are estimated using linear regression.

In Vivo MMP Inhibition Test Procedure

A 2 cm piece of dialysis tubing (molecular weight cut-off 12–14,000, 10 mm flat width) containing matrix metalloproteinase enzyme (stromelysin, collagenase or gelatinase in 0.5 mL of buffer) is implanted either ip or sc (in the back) of a rat (Sprague-Dawley, 150–200 g) or mouse (CD-1, 25–50 g) under anesthesia. Drugs are administered PO, IP, SC or IV through a canula in the jugular vein. Drugs are administered in a dose volume of 0.1 to 0.25 mL/animal. Contents of the dialysis tubing is collected and enzyme activity assayed.

Enzyme reaction rates for each dialysis tube are calculated. Tubes from at least 3 different animals are used to calculate the mean±sem. Statistical significance (p<0.05) of vehicle-treated animals versus drug-treated animals is determined by analysis of variance. (*Agents and Actions* 21: 331, 1987).

Test Procedure for Measuring TACE Inhibition

Using 96-well black microtiter plates, each well receives a solution composed of 10 μL TACE (final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generate using multiple doses of drug and $IC_{50}$ values with 95% CI are estimated using linear regression.

Results of the above in-vitro and in-vivo matrix metalloproteinase inhibition and TACE inhibition standard pharmacological test procedures are given in Table I below.

TABLE I

Inhibition of MMP and TACE

| Example | MMP-1[1] | MMP-9[1] | MMP-13[1] | TACE[1] | in-vivo MMP[2] |
|---|---|---|---|---|---|
| 11 | 172 | 11 | 7 | >1000 | |
| 12 | 933 | 2 | 1 | 190 | |
| 13 | 82 | 15 | 9 | 3% | |
| 14 | 108 | 8 | 6 | 24% | |
| 15 | 139 | 25 | 12 | 7% | |
| 16 | 99 | 6 | 3 | 36% | 64%(100) |
| 17 | 3100 | 8 | 16 | 401 | |
| 18 | 152 | | 26 | 627 | |
| 19 | 194 | 2 | 4 | 314 | |
| 20 | 344 | 6 | 9 | 589 | |
| 29 | 200 | 5 | 4 | | |
| 30 | 22 | 11 | 467 | 47 | |
| 31 | 225 | 2 | 2 | 80 | |
| 32 | 456 | 1 | 1 | 24 | |
| 33 | 1012 | 1 | 1 | | |
| 34 | 301 | 9 | 12 | 20 | |
| 35 | 234 | 4 | 5 | 49 | |
| 36 | 46 | 2 | 1 | 226 | 81%(50) |
| 37 | 65 | 2 | 1 | 124 | |
| 38 | 100 | 4 | 3 | 336 | |
| 39 | 75 | 2 | 2 | 53 | |
| 40 | 151 | 3 | 4 | 120 | |
| 41 | 136 | 2 | 2 | 161 | 65%(50) |
| 42 | 5200 | 874 | 37 | 16% | |
| 43 | 43% | 71% | 63% | 20% | |
| 44 | 65% | 59% | 73% | 5% | |
| 52 | 45 | 2.4 | 1.4 | 236 | 74%(100) |
| 60 | 39 | 2.9 | 2.5 | 160 | 53%(50) |
| 61 | 36 | 2.3 | 2.3 | 214 | 72%(50) |
| 62 | 1236 | 5.7 | 23 | 46% | |
| 63 | 721 | 6.8 | 23 | | |
| 64 | 913 | 5.5 | 19 | | |
| 66 | 512 | 0.81 | 0.27 | | 5%(25) |
| 67 | 96 | 3.0 | 2.4 | 138 ± 11 | |
| 68 | 96 | 3.0 | 2.4 | 115 ± 5 | 80%(50) |
| 86 | 131 | 6.9 | 10.0 | 118 ± 6 | |
| 87 | 111 | 8.9 | 10 | 147 ± 5 | 12%(25) |
| 88 | 643 | 10.4 | 18.7 | 40.5% | |
| 89 | 116 | 0.8 | 1.1 | 356 ± 15 | 6%(25) |
| 90 | 550 | 2.3 | 3.0 | 535 ± 77 | 39%(25) |
| 91 (HCl) | 1805 | 1.8 | 1.1 | 38.7% | 54%(25) |
| 92 | 60.2% at 10 μM | 12.0 | 6.1 | >1644 | 30%(25) |
| 93 | 8786 | 10.1 | 3.9 | 34.9% | 49%(25) |
| 94 | 2548 | 3.0 | 3.2 | 41.6% | 12%(25) |

[1]$IC_{50}$ nM or % inhibition at 1 μM concentration
[2]% inhibition (dose, mg/kg), p.o. vs MMP-13

Based on the results obtained in the standard pharmacological test procedures described above, the compounds of this invention were shown to be inhibitors of the enzymes MMP-1, MMP-9, MMP-13 and TNF-α converting enzyme (TACE) and are therefore useful in the treatment of disorders such as arthritis, tumor metastasis, tissue ulceration, abnormal wound healing, periodontal disease, graft rejection, insulin resistance, bone disease and HIV infection.

The compounds of this invention are also useful in treating or inhibiting pathological changes mediated by matrix metalloproteinases such as atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles. Projected oral daily dosages are 2–500 mg/kg, preferred oral daily dosages are 2–50 mg/kg, and more preferred oral daily dosages are 5–25 mg/kg.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:

1. A compound having the formula:

B wherein

B is

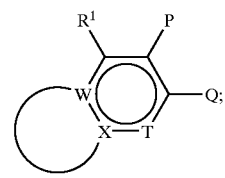

P and Q are

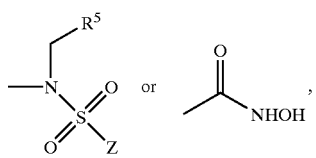

provided that when P is

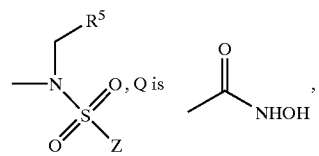

and vice versa;

T, W, and X are each, independently, carbon or nitrogen, provided that when T is carbon, it may be optionally substituted with $R^1$; and provided that no more than 2 of T, W, and X are nitrogen;

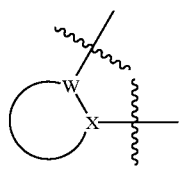

is a phenyl ring or is a heteroaryl ring of ring 5–6 atoms which may contain 0–2 heteratoms selected from nitrogen, oxygen, and sulfur, in addition to any heteroatoms defined by W or X; wherein the phenyl or heteroaryl ring may be optionally mono-, di-, or tri-substituted with $R^1$;

Z is a phenyl, naphthyl, heteroaryl, or heteroaryl fused to phenyl, wherein the heteroaryl moiety contains of 5–6 ring atoms and 1–3 heteroatoms selected from nitrogen, oxygen, or sulfur; wherein the phenyl, naphthyl, heteroaryl, or phenyl fused heteroaryl moieties may be optionally mono-, di-, or tri-substituted with $R^1$;

$R^1$ is hydrogen, halogen, alkyl of 1–8 carbon atoms, alkenyl of 2–6 carbon atoms, alkynyl of 2–6 carbon atoms, cycloalkyl of 3–6 carbon atoms, —$(CH_2)_nZ$, —$OR^2$, —CN, —$COR^2$, perfluoroalkyl of 1–4 carbon atoms, —$CONR^2R^3$, —$S(O)_xR^2$ —$OPO(OR^2)OR^3$, —$PO(OR^2)R^3$, —$OC(O)NR^2R^3$, —$COOR^2$, —$CONR^2R^3$, —$SO_3H$, —$NR^2R^3$, —$NR^2COR^3$, —$NR^2COOR^3$, —$SO_2NR^2R^3$, —$NO_2$, —$N(R^2)SO_2R^3$, —$NR_2ONR^2R^3$, —$NR^2C(=NR^3)NR^2R^3$, —$SO_2NHCOR^4$, —$CONHSO_2R^4$, -tetrazol-5-yl, —$SO_2NHCN$, —$SO_2NHCONR^2R^3$, or Z;

V is a saturated or partially unsaturated heterocycloalkyl ring of 5–7 ring atoms having 1–3 heteroatoms selected from N, O, or S, which may be optionally mono-, or di-substituted with $R^2$;

$R^2$ and $R^3$ are each, independently, hydrogen, alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;

$R^4$ is alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;

$R^5$ is hydrogen, alkyl of 1–8 carbon atoms, alkenyl of 2–6 carbon atoms, alkynyl of 2–6 carbon atoms, Z, or V;

n=1–6;

X=0–2 or a pharmaceutically acceptable salt thereof.

2. The compound according to claim 1, wherein P is

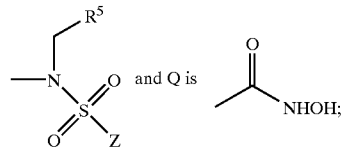

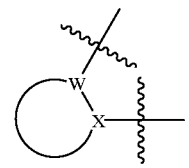

is phenyl or pyrazole, each optionally mono-, di-, or tri-substituted with $R^1$;

or a pharmaceutically acceptable salt thereof.

3. A method of inhibiting pathological changes mediated by matrix metalloproteinases in a mammal in need thereof which comprises providing to said mammal a therapeutically effective amount of a compound having the formula:

B wherein

B is

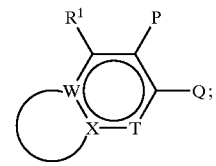

P and Q are

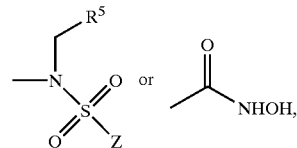

provided that when P is

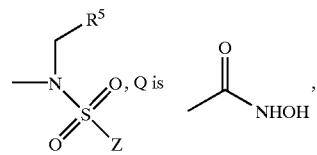

and vice versa;

T, W, and X are each, independently, carbon or nitrogen, provided that when T is carbon, it may be optionally substituted with $R^1$; and provided that no more than 2 of T, W, and X are nitrogen;

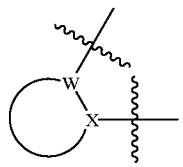

is a phenyl ring or is a heteroaryl ring of ring 5–6 atoms which may contain 0–2 heteroatoms selected from nitrogen, oxygen, and sulfur, in addition to any heteroatoms defined by W or X; wherein the phenyl or heteroaryl ring may be optionally mono-, di-, or tri-substituted with $R^1$;

Z is a phenyl, naphthyl, heteroaryl, or heteroaryl fused to phenyl, wherein the heteroaryl moiety contains of 5–6 ring atoms and 1–3 heteroatoms selected from nitrogen, oxygen, or sulfur; wherein the phenyl, naphthyl, heteroaryl, or phenyl fused heteroaryl moieties may be optionally mono-, di-, or tri-substituted with $R^1$;

$R^1$ is hydrogen, halogen, alkyl of 1–8 carbon atoms, alkenyl of 2–6 carbon atoms, alkynyl of 2–6 carbon atoms, cycloalkyl of 3–6 carbon atoms, —$(CH_2)_nZ$, —$OR^2$, —CN, —$COR^2$, perfluoroalkyl of 1–4 carbon atoms, —$CONR^2R^3$, —$S(O)_xR^2$ —$OPO(OR^2)OR^3$, —$PO(OR^2)R^3$, —$OC(O)NR^2R^3$, —$COOR^2$, —$CONR^2R^3$, —$SO_3H$, —$NR^2R^3$, —$NR^2COR^3$, —$NR^2COOR^3$, —$SO_2NR^2R^3$, —$NO_2$, —$N(R^2)SO_2R^3$, —$NR^2CONR^2R^3$, —$NR^2C(=NR^3)NR^2R^3$, or Z;

V is a saturated or partially unsaturated heterocycloalkyl ring of 5–7 ring atoms having 1–3 heteroatoms selected from N, O, or S, which may be optionally mono-, or di-substituted with $R^2$;

$R^2$ and $R^3$ are each, independently, hydrogen, alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;

$R^4$ is alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;

$R^5$ is hydrogen, alkyl of 1–8 carbon atoms, alkenyl of 2–6 carbon atoms, alkynyl of 2–6 carbon atoms, Z, or V;

n=1–6;

X=0–2 or a pharmaceutically acceptable salt thereof.

4. The method according to claim 3 wherein the matrix metalloproteinase mediated condition treated is atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, or periodontal disease.

5. The method according to claim 3, wherein the matrix metalloproteinase mediated condition treated is age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

6. A method of inhibiting pathological changes mediated by TNF-α converting enzyme (TACE) in a mammal in need thereof, which comprises providing to said mammal a therapeutically effective amount of a compound having the formula:

B wherein

B is

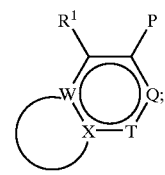

P and Q are

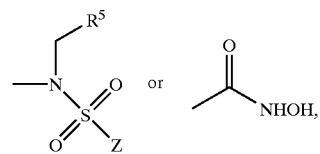

provided that when P is

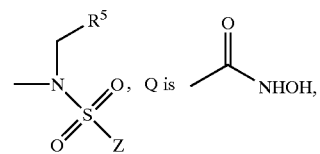

and vice versa;

T, W, and X are each; independently, carbon or nitrogen, provided that when T is carbon, it may be optionally substituted with $R^1$; and provided that no more than 2 of T, W, and X are nitrogen;

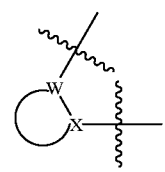

is a phenyl ring or is a heteroaryl ring of ring 5–6 atoms which may contain 0–2 heteroatoms selected from nitrogen, oxygen, and sulfur, in addition to any heteroatoms defined by W or X; wherein the phenyl or heteroaryl ring may be optionally mono-, di-, or tri-substituted with $R^1$;

Z is a phenyl, naphthyl, heteroaryl, or heteroaryl fused to phenyl, wherein the heteroaryl moiety contains of 5–6 ring atoms and 1–3 heteroatoms selected from nitrogen, oxygen, or sulfur; wherein the phenyl, naphthyl, heteroaryl, or phenyl fused heteroaryl moieties may be optionally mono-, di-, or tri-substituted with $R^1$;

$R^1$ is hydrogen, halogen, alkyl of 1–8 carbon atoms, alkenyl of 2–6 carbon atoms, alkynyl of 2–6 carbon atoms, cycloalkyl of 3–6 carbon atoms, —$(CH_2)_nZ$, —$OR^2$, —CN, —$COR^2$, perfluoroalkyl of 1–4 carbon atoms, —$CONR^2R^3$, —$S(O)_xR^2$ —$OPO(OR^2)OR^3$, —$PO(OR^2)R^3$, —$OC(O)NR^2R^3$, —$COOR^2$, —$CONR^2R^3$, —$SO_3H$, —$NR^2R^3$, —NR $COR^3$, —$NR^2COOR^3$, —$SO_2NR^2R^3$, —$NO_2$, —$N(R^2)SO_2R^3$, —$NR^2CONR^2R^3$, —$NR^2C(=NR^3)NR^2R^3$, —$SO_2NHCOR^4$, —$CONHSO_2R^4$, -tetrazol-5-yl, —$SO_2NHCN$, —$SO_2NHCONR^2R^3$, or Z;

V is a saturated or partially unsaturated heterocycloalkyl ring of 5–7 ring atoms having 1–3 heteroatoms selected from N, O, or S, which may be optionally mono-, or di-substituted with $R^2$;

$R^2$ and $R^3$ are each, independently, hydrogen, alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;

$R^4$ is alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;

$R^5$ is hydrogen, alkyl of 1–8 carbon atoms, alkenyl of 2–6 carbon atoms, alkynyl of 2–6 carbon atoms, Z, or V;

n=1–6;

X=0–2 or a pharmaceutically acceptable salt thereof.

7. The method according to claim 6 wherein the condition treated is rheumatoid arthritis, graft rejection, cachexia, anorexia, inflammation, fever, insulin resistance, septic shock, congestive heart failure, inflammatory disease of the central nervous system, inflammatory bowel disease, or HIV infection.

8. A pharmaceutical composition comprising a compound having the formula:

B wherein

B is

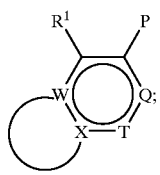

P and Q are

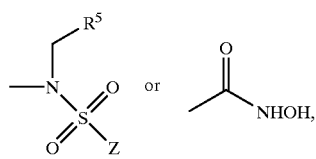

provided that when P is

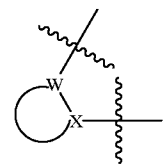, Q is 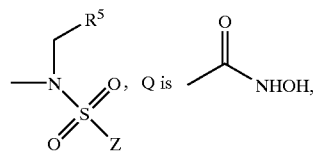

and vice versa;

T, W, and X are each, independently, carbon or nitrogen, provided that when T is carbon, it may be optionally substituted with $R^1$; and provided that no more than 2 of T, W, and X are nitrogen;

is a phenyl ring or is a heteroaryl ring of ring 5–6 atoms which may contain 0–2 heteratoms selected from nitrogen, oxygen, and sulfur, in addition to any heteroatoms defined by W or X; wherein the phenyl or heteroaryl ring may be optionally mono-, di-, or tri-substituted with $R^1$;

Z is a phenyl, naphthyl, heteroaryl, or heteroaryl fused to phenyl, wherein the heteroaryl moiety contains of 5–6 ring atoms and 1–3 heteroatoms selected from nitrogen, oxygen, or sulfur; wherein the phenyl, naphthyl, heteroaryl, or phenyl fused heteroaryl moieties may be optionally mono-, di-, or tri-substituted with $R^1$;

$R^1$ is hydrogen, halogen, alkyl of 1–8 carbon atoms, alkenyl of 2–6 carbon atoms, alkynyl of 2–6 carbon atoms, cycloalkyl of 3–6 carbon atoms, —$(CH_2)_nZ$, —$OR^2$, —CN, —$COR^2$, perfluoroalkyl of 1–4 carbon atoms, —$CONR^2R^3$, —$S(O)_xR^2$ —$OPO(OR^2)OR^3$, —$PO(OR^2)R^3$, —$OC(O)NR^2R^3$, —$COOR^2$, —$CONR^2R^3$, —$SO_3H$, —$NR^2R^3$, —$NR^2COR^3$, —$NR^2COOR^3$, —$SO_2NR^2R^3$, —$NO_2$, —$N(R^2)SO_2R^3$, —$NR^2CONR^2R^3$, —$NR^2C(=NR^3)NR^2R^3$, —$SO_2NHCOR^4$, —$CONHSO_2R^4$, -tetrazol-5-yl, —$SO_2NHCN$, —$SO_2NHCONR^2R^3$, or Z;

V is a saturated or partially unsaturated heterocycloalkyl ring of 5–7 ring atoms having 1–3 heteroatoms selected from N, O, or S, which may be optionally mono-, or di-substituted with $R^2$;

$R^2$ and $R^3$ are each, independently, hydrogen, alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;

$R^4$ is alkyl of 1–8 carbon atoms, alkenyl of 2–6 carbon atoms, alkynyl of 2–6 carbon atoms, cycloalkyl of 3–6 carbon atoms; perfluoroalkyl of 1–4 carbon atoms, Z or V;

$R^5$ is hydrogen, alkyl of 1–8 carbon atoms, alkenyl of 2–6 carbon atoms, alkynyl of 2–6 carbon atoms, Z, or V;

n=1–6;

X=0–2 or a pharmaceutically acceptable salt thereof, and a pharmaceutical carrier.

* * * * *

UNITED STATES PATENT AND TRADEMARK OFFICE
CERTIFICATE OF CORRECTION

PATENT NO. : 6,498,167 B2
DATED : March 11, 2003
INVENTOR(S) : Jeremy I. Levin et al.

It is certified that error appears in the above-identified patent and that said Letters Patent is hereby corrected as shown below:

<u>Column 57,</u>
Line 53, change "–$NR_2ONR^2R^3$" to -- –$NR^2CONR^2R^3$ --

<u>Column 61,</u>
Line 10, change "-$NRCOR^3$" to -- -$NR^2COR^3$ --

Signed and Sealed this

Fifteenth Day of July, 2003

JAMES E. ROGAN
*Director of the United States Patent and Trademark Office*